US011219659B2

(12) United States Patent
Chengappa et al.

(10) Patent No.: US 11,219,659 B2
(45) Date of Patent: Jan. 11, 2022

(54) METHODS AND COMPOSITIONS FOR TREATING SCHIZOPHRENIA AND SCHIZOAFFECTIVE DISORDERS

(71) Applicant: University of Pittsburgh—Of the Commonwealth System of Higher Education, Pittsburgh, PA (US)

(72) Inventors: Kadiamada N. Chengappa, Pittsburgh, PA (US); Dean Francis Salisbury, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/775,565

(22) PCT Filed: Sep. 6, 2017

(86) PCT No.: PCT/US2017/050234
§ 371 (c)(1),
(2) Date: May 11, 2018

(87) PCT Pub. No.: WO2018/156202
PCT Pub. Date: Aug. 30, 2018

(65) Prior Publication Data
US 2020/0197473 A1 Jun. 25, 2020

Related U.S. Application Data

(60) Provisional application No. 62/463,836, filed on Feb. 27, 2017.

(51) Int. Cl.
*A61K 36/81* (2006.01)
*A61P 25/18* (2006.01)
*A61K 31/585* (2006.01)
*A61K 47/26* (2006.01)

(52) U.S. Cl.
CPC ............ *A61K 36/81* (2013.01); *A61K 31/585* (2013.01); *A61K 47/26* (2013.01); *A61P 25/18* (2018.01)

(58) Field of Classification Search
None
See application file for complete search history.

(56) References Cited

U.S. PATENT DOCUMENTS

| | | | |
|---|---|---|---|
| 6,153,198 A * | 11/2000 | Ghosal | A61K 36/81 424/773 |
| 6,713,092 B1 | 3/2004 | Ghosal | |
| 7,250,181 B2 | 7/2007 | Ghosal | |
| 7,318,938 B2 | 1/2008 | Ghosal | |
| 8,815,933 B2 | 8/2014 | Chesworth et al. | |
| 2002/0040058 A1 | 4/2002 | Kiliaan et al. | |
| 2004/0166184 A1 | 8/2004 | Ghosal | |
| 2005/0059727 A1 * | 3/2005 | Nair | A61P 3/00 514/414 |
| 2007/0122485 A1 | 5/2007 | Petersen et al. | |
| 2007/0122495 A1 * | 5/2007 | Managoli | A61K 36/84 424/725 |
| 2011/0229591 A1 | 9/2011 | Ravindranath et al. | |
| 2013/0115316 A1 | 5/2013 | Ghosal et al. | |
| 2013/0261068 A1 | 10/2013 | Ghosal et al. | |
| 2015/0283193 A9 | 10/2015 | McCord et al. | |
| 2015/0320771 A1 * | 11/2015 | Ghosal | A61P 25/24 514/175 |
| 2015/0320814 A1 * | 11/2015 | Patel | A61K 36/38 424/682 |

FOREIGN PATENT DOCUMENTS

| | | |
|---|---|---|
| EP | 1569669 A2 | 9/2005 |
| IN | 01513MU2012 A | 5/2014 |
| IN | 1513MUM/2012 A * | 5/2014 |

OTHER PUBLICATIONS

White P. et al. Natural Withanolides in the Treatment of Chronic Diseases. Advances in Experimental Medicine & Biology 928:329-373, 2016. (Year: 2016).*
Tohda, C. et al. Scientific Basis for the Anti-Dementia Drugs of Consituents from Ashwagandha. J of Traditional Medicines 22(Suppl 1)176-182, 2005. (Year: 2005).*
Chengappa K. et al. Adjunctive Use of a Standardized extract of Withania somnifera to Treat Symptom Exacerbation in Schizophrenia. J Clinical Psychiatry 79(5)1-17 Sep./Oct. 2018. (Year: 2018).*
Gannon J. et al. Effects of a Standardized Extract of Withania somnifera on Depression and Anxiety Symptoms in Persons with Schizophrenia . . . Anals of Clinical Psychiatry 31(2)123-129, May 2019. (Year: 2019).*
Mulabagal et al., "Withanolide Sulfoxide from Aswagandha Roots Inhibits Nuclear Transcription Factor-Kappa-B, Cyclooxygenase and Tumor Cell Proliferation", Phytother Res, 2009, pp. 987-992, vol. 22.
Muller, "COX-2 inhibitors as antidepressants and antipsychotics: Clinical evidence", Current Opinion in Investigational Drugs, 2010, pp. 31-42, vol. 11:1.
Muller et al., "Beneficial Antipsychotic Effects of Celecoxib Add-On Therapy Compared to Risperidone Alone in Schizophrenia", Am J Psychiatry, 2002, pp. 1029-1034, vol. 159.
Muller et al., "COX-2 inhibition as a treatment approach in schizophrenia: Immunological considerations and clinical effects of celecoxib add-on therapy", Eur Arch Psychiatry Clin Neurosci, 2004, pp. 14-22, vol. 254.

(Continued)

*Primary Examiner* — Ralph J Gitomer
(74) *Attorney, Agent, or Firm* — The Webb Law Firm

(57) ABSTRACT

Provided herein are methods of treatment of psychiatric disorders requiring treatment with an antipsychotic drug, such as schizophrenia or schizoaffective disorder, comprising administration of both the antipsychotic drug and a *W. somnifera* plant part, extract, chemical constituent(s) thereof, or a derivative thereof to treat symptoms of the psychiatric disorder. Treatment is typically continued for at least four weeks. A combination dosage form comprising both the antipsychotic drug and the *W. somnifera* plant part, extract, chemical constituent(s) thereof, or a derivative thereof in amounts effective to treat the psychiatric disorder.

18 Claims, 17 Drawing Sheets

(56) References Cited

OTHER PUBLICATIONS

Muller et al., "Schizophrenia as an Inflammation-Mediated Dysbalance of Glutamatergic Neurotransmission", Neurotoxicity Research, 2006, pp. 131-148, vol. 10:2.
Muller et al., "Immune System and Schizophrenia", Curr Immunol Rev., 2010, pp. 213-220, vol. 6:3.
Muller et al., "Kynurenine Pathway in Schizophrenia: Pathophysiological and Therapeutic Aspects", Current Pharmaceutical Design, 2011, pp. 130-136, vol. 17.
Naatanen et al., "Central auditory dysfunction in schizophrenia as revealed by the mismatch negativity (MMN) and its magnetic equivalent MMNm: a review", International Journal of Neuropsychopharmacology, 2009, pp. 125-135, vol. 12.
Naatanen et al., "Mismatch negativity (MMN) as biomarker predicting psychosis in clinically at-risk individuals", Biological Psychology, 2016, pp. 36-40, vol. 116.
Naidu et al., "Effect of Withania somnifera Root Extract on Reserpine-induced Orofacial Dyskinesia and Cognitive Dysfunction", Phytother. Res., 2006, pp. 140-146, vol. 20.
Narinderpal et al., "Research and Reviews: Journal of Botanical Sciences", RRJBS, 2013, pp. 6-14, vol. 2:4.
Nashine et al., "Role of inflammatory mediators in anti-inflammatory activity of Withania Somnifera on chronic inflammatory reaction", Indian Vet Med, 1995, pp. 286-288, vol. 19, Abstract only.
Nitta et al., "Adjunctive Use of Nonsteroidal Anti-inflammatory Drugs for Schizophrenia: A Meta-analytic Investigation of Randomized Controlled Trials", Schizophrenia Bulletin, 2013, pp. 1230-1241, vol. 39:6.
Oades et al., "Auditory event-related potential (ERP) and difference-wave topography in schizophrenic patients with/without active hallucinations and delusions: a comparison with young obsessive-compulsive disorder (OCD) and healthy subjects", International Journal of Psychophysiology, 1996, pp. 185-214, vol. 22.
O'Donnell et al., "Dysfunctions in Multiple Interrelated Systems as the Neurobiological Bases of Schizophrenic Symptom Clusters", Schizophrenia Bulletin, 1998, pp. 267-283, vol. 24:2.
Olney et al., "Glutamate Receptor Dysfunction and Schizophrenia", Arch Gen Psychiatry, 1995, pp. 998-1007, vol. 52.
Pafundo et al., "Cholinergic modulation of neuronal excitability and recurrent excitation-inhibition in prefrontal cortex circuits: implications for gamma oscillations", J Physiol, 2013, pp. 4725-4748, vol. 591:19.
Pawlowski et al., "Phencyclidine activates rat A10 dopamine neurons but reduces burst activity and causes regularization of firing", Acta Physiol Scand, 1990, pp. 529-530, vol. 139.
Perez et al., "Mismatch Negativity is a Sensitive and Predictive Biomarker of Perceptual Learning During Auditory Cognitive Training in Schizophrenia", Neuropsychopharmacology, 2017, pp. 2206-2213, vol. 42.
Perlman et al., "Clinical Significance of Auditory Target P300 Subcomponents in Psychosis: Differential Diagnosis, Symptoms Profiles, and Course", Schizophr Res., 2015, pp. 145-151, vol. 165:0.
Pingali et al., "Effect of standardized aqueous extract of Withania somnifera on tests of cognitive and psychomotor performance in healthy human participants", Pharmacognosy Res, 2014, pp. 12-18, vol. 6:1.
Politi et al., "Increased Proapoptotic Serum Activity in Patients with Chronic Mood Disorders", Archives of Medical Research, 2008, pp. 242-245, vol. 39.
Potvin et al., "Inflammatory Cytokine Alterations in Schizophrenia: A Systematic Quantitative Review", Biol Psychiatry, 2008, pp. 801-808, vol. 63.
Prakash et al., "Withania somnifera Alleviates Parkinsonian Phenotypes by Inhibiting Apoptotic Pathways in Dopaminergic Neurons", Neurochem Res, 2014, pp. 2527-2536, vol. 39.
Peuskens et al., "Effects of risperidone on affective symptoms in patients with schizophrenia", International Clinical Psychopharmacology, 2000, pp. 343-349, vol. 15.
Ramakanth et al., "A randomized, double blind placebo controlled study of efficacy and tolerability of Withania somnifera extracts in knee joint pain", Journal of Ayurveda and Integrative Medicine, 2016, pp. 151-157, vol. 7.
Rao et al., "Smaller Auditory P300 Amplitude in Schizophrenics in Remission", Neuropsychobiology, 1995, pp. 171-174, vol. 32, Abstract only.
Rapaport et al., "Celecoxib Augmentation of Continuously Ill Patients with Schizophrenia", Biol Psychiatry, 2005, pp. 1594-1596, vol. 57.
Rapaport et al., "Serial Mitogen-Stimulated Cytokine Production from Continuously Ill Patients with Schizophrenia", Neuropsychopharmacology, 2010, pp. 428-434, vol. 35.
Reddy et al., "Enzymes of the Antioxidant Defense System in Chronic Schizophrenic Patients", Biol Psychiatry, 1991, pp. 409-412, vol. 30.
Roth et al., "Some Features of the Auditory Evoked Response in Schizophrenics", Arch Gen Psychiat, 1972, pp. 466-471, vol. 27.
Rothermundt et al., "Review of Immunological and Immunopathological Findings in Schizophrenia", Brain, Behavior, and Immunity, 2001, pp. 319-339, vol. 15.
Saddadi et al., "The Effect of Treatment with N-acetylcysteine on the Serum Levels of C-reactive Protein and Interleukin-6 in Patients on Hemodialysis", Saudi J Kidney Dis Transpl, 2014, pp. 66-72, vol. 25:1.
Salisbury et al., "First-Episode Schizophrenic Psychosis Differs From First-Episode Affective Psychosis and Controls in P300 Amplitude Over Left Temporal Lobe", Arch Gen Psychiatry, 1998, pp. 173-180, vol. 55.
Salisbury et al., "P300 Topography Differs in Schizophrenia and Manic Psychosis", Biol Psychiatry, 1999, pp. 98-106, vol. 45.
Sathyasaikumar et al., "Impaired Kynurenine Pathway Metabolism in the Prefrontal Cortex of Individuals With Schizophrenia", Schizophrenia Bulletin, 2011, pp. 1147-1156, vol. 37:6.
Sato et al., "Impairment in activation of a frontal attention-switch mechanism in schizophrenic patients", Biological Psychology, 2002, pp. 49-63, vol. 62.
Schall et al., "The effect of clozapine therapy on frontal lobe dysfunction in schizophrenia: neuropsychology and event-related potential measures", International Journal of Neuropsychopharmacology, 1998, pp. 19-29, vol. 1.
Schumberg et al., "Serum S100B Is Related to Illness Duration and Clinical Symptoms in Schizophrenia—A Meta-Regression Analysis", Front. Cell. Neurosci, 2016, pp. 1-11, vol. 10:46.
Schwarz et al., "T-helper-1 and T-helper-2 Responses in Psychiatric Disorders", Brain, Behavior, and Immunity, 2001, pp. 340-370, vol. 15.
Shapiro et al., "Aripiprazole, A Novel Atypical Antipsychotic Drug with a Unique and Robust Pharmacology", Neuropsychopharmacology, 2003, pp. 1400-1411, vol. 28.
Sheehan et al., "The Mini-International Neuropsychiatric Interview (M.I.N.I.): The Development and Validation of a Structured Diagnostic Psychiatric Interview for DSM-IV and ICD-10", J Clin Psychiatry, 1998, pp. 22-23, vol. 59.
Singh et al., "Withania somnifera inhibits NF-kB and AP-1 Transcription Factors in Human Peripheral Blood and Synovial Fluid Mononuclear Cells", Phytother. Res., 2007, pp. 905-913, vol. 21.
Singh et al., "Meta-Analysis of the Efficacy of Adjunctive NMDA Receptor Modulators in Chronic Schizophrenia", CNS Drugs, 2011, pp. 859-885, vol. 25:10.
Snyder, "Dopamine Receptors, Neuroleptics, and Schizophrenia", Am J Psychiatry, 1981, pp. 460-464, vol. 138:4.
Soman et al., "Oxidative Stress Induced NMDA Receptor Alteration Leads to Spatial Memory Deficits in Temporal Lobe Epilepsy: Ameliorative Effects of Withania somnifera and Withanolide A", Neurochem Res, 2012, pp. 1915-1927, vol. 37.
Spencer et al., "γ-Band Auditory Steady-State Responses Are Impaired in First Episode Psychosis", Biol Psychiatry, 2008, pp. 369-375, vol. 64.
Stern et al., "Limitations of Controlled Augmentation Trials in Schizophrenia", Biol Psychiatry, 1997, pp. 138-143, vol. 42.

(56) References Cited

OTHER PUBLICATIONS

Steullet et al., "Redox dysregulation, neuroinflammation, and NMDA receptor hypofunction: a "central hub" in schizophrenia pathophysiology?", Schizophr Res., 2016, pp. 41-51, vol. 176:1.
Subbaraju et al., "Ashwagandhanolide, a Bioactive Dimeric Thiowithanolide Isolated from the Roots of Withania somnifera", J. Nat. Prod., 2006, pp. 1790-1792, vol. 69.
Sullivan et al., "Inhibitory Interneurons, Oxidative Stress, and Schizophrenia", Schizophrenia Bulletin, 2012, pp. 373-376, vol. 38:3.
Sumiyoshi et al., "Neural basis for the ability of atypical antipsychotic drugs to improve cognition in schizophrenia", Frontiers in Behavioral Neuroscience, 2013, pp. 1-8, vol. 7:140.
Sun et al., "Gamma oscillations in schizophrenia: Mechanisms and clinical significance", Brain Research, 2011, pp. 98-114, vol. 1413.
Sun et al., "Withania somnifera and Its Withanolides Attenuate Oxidative and Inflammatory Responses and Up-Regulate Antioxidant Responses in BV-2 Microglial Cells", Neuromol Med, 2016, pp. 241-252, vol. 18.
Torrey et al., "Cytomegalovirus Antibody in Cerebrospinal Fluid of Schizophrenic Patients Detected by Enzyme Immunoassay", Science, 1982, pp. 892-894, vol. 216:4548.
Toyomaki et al., "Tone duration mismatch negativity deficits predict impairment of executive function in schizophrenia", Progress in Neuro-Psychopharmacology & Biological Psychiatry, 2008, pp. 95-99, vol. 32.
Turetsky et al., "P300 Subcomponent Abnormalities in Schizophrenia: I. Physiological Evidence for Gender and Subtype Specific Differences in Regional Pathology", Biol Psychiatry, 1998, pp. 84-96, vol. 43.
Umbricht et al., "Effects of Clozapine on Auditory Event-Related Potentials in Schizophrenia", Biol Psychiatry, 1998, pp. 716-725, vol. 44.
Umbricht et al., "Effects of risperidone on auditory event-related potentials in schizophrenia", International Journal of Neuropsychopharmacology, 1999, pp. 299-304, vol. 2.
Umbricht et al., "Mismatch Negativity Predicts Psychotic Experiences Induced by NMDA Receptor Antagonist in Healthy Volunteers", Biol Psychiatry, 2002, pp. 400-406, vol. 51.
Umbricht et al., "Mismatch negativity in schizophrenia: a meta-analysis". Schizophrenia Research, 2005, pp. 1-23, vol. 76.
Valko et al., "Free radicals and antioxidants in normal physiological functions and human disease", The International Journal of Biochemistry & Cell Biology, 2007, pp. 44-84, vol. 39.
Van Berckel et al., "Microglia Activation in Recent-Onset Schizophrenia: A Quantitative (R)-[11C]PK11195 Positron Emission Tomography Study", Biol Psychiatry, 2008, pp. 820-822, vol. 64.
Van Kammen et al., "Relationship between immune and behavioral measures in schizophrenia", Current Update in Psychoimmunology, New York, Springer, 1997, pp. 51-55.
Villemain et al., "Aberrant T Cell-Mediated Immunity in Untreated Schizophrenic Patients: Deficient Interleukin-2 Production", Am J Psychiatry, 1989, pp. 609-616, vol. 146.
Wanaverbecq et al., "Cholinergic Axons Modulate GABAergic Signaling among Hippocampal Interneurons via Postsynaptic a7 Nicotinic Receptors", J Neurosci., 2007, pp. 5683-5693, vol. 27:21.
Wilke et al., "Investigations of cytokine production in whole blood cultures of paranoid and residual schizophrenic patients", Eur Arch Psychiatry Clin Neurosci, 1996, pp. 279-284, vol. 246.
Yadav et al., "Propoxur-induced acetylcholine esterase inhibition and impairment of cognitive function: Attenuation by Withania somnifera", Indian Journal of Biochemistry & Biophysics, 2010, pp. 117-120, vol. 47.
Yao et al., "Antioxidants, Redox Signaling, and Pathophysiology in Schizophrenia: An Integrative View", Antioxid. Redox Signal., 2011, pp. 2011-2035, vol. 15.
Yefet et al., "Impairments of event-related magnetic fields in schizophrenia patients with predominant negative symptoms", Psychiatry Research: Neuroimaging, 2015, pp. 325-332, vol. 231.

Yolken et al., "Viruses, Schizophrenia, and Bipolar Disorder", Clinical Microbiology Reviews, 1995, pp. 131-145, vol. 8:1.
Zafarullah et al., "Molecular mechanisms of N-acetylcysteine actions", CMLS. Cell. Mol. Life Sci., 2003, pp. 6-20, vol. 60.
Zhou et al., "Effect of Aripiprazole on Mismatch Negativity (MMN) in Schizophrenia", PLOS One, 2013, pp. 1-7, vol. 8:1.
Aalto et al., "Cortical glutamate-dopamine interaction and ketamine-induced psychotic symptoms in man", Psychopharmacology, 2005, pp. 375-383, vol. 182.
Agarwal et al., "Studies on immunomodulatory activity of *Withania somnifera* (Ashwagandha) extracts in experimental immune inflammation", Journal of Ethnopharmacology, 1999, pp. 27-35, vol. 67.
Agnihotri et al, "Effects of Withania somnifera in patients of schizophrenia: A randomized, double blind, placebo controlled pilot trial study", Indian J Pharmacol, 2013, pp. 417-418, vol. 45:4.
Ajit et al., "Phytochemicals and botanical extracts regulate NF-kB and Nrf2/ARE reporter activities in DI TNC1 astrocytes", Neurochem Int., 2016, pp. 49-56, vol. 97.
Akhondzadeh et al., "Celecoxib as adjunctive therapy in schizophrenia: A double-blind, randomized and placebo-controlled trial", Schizophrenia Research, 2007, pp. 179-185, vol. 90.
Anbalagan et al., "Influence of an Indian Medicine (Ashwagandha) on Acute-Phase Reactants in Inflammation", Indian Journal of Experimental Biology, 1981, pp. 245-249, vol. 19.
Anbalagan et al., "*Withania somnifera* (Ashwagandha), a Rejuvenating Herbal Drug Which Controls Alpha-2-Macroglobulin Synthesis During Inflammation", International Journal of Crude Drug Research, 1985, pp. 177-183, vol. 23:4, Abstract only.
Andrade et al., "A Double-Blind, Placebo-Controlled Evaluation of the Anxiolytic Efficacy of an Ethanolic Extract of Withania Somnifera", Indian Journal of Psychiatry, 2000, pp. 295-301, vol. 42:3.
Anis et al., "The dissociative anaesthetics, ketamine and phencyclidine, selectively reduce excitation of central mammalian neurones by N-methyl-aspartate", Br. J. Pharmac., 1983, pp. 565-575, vol. 79.
Baldeweg et al., "Impairment in frontal but not temporal components of mismatch negativity in schizophrenia", International Journal of Psychophysiology, 2002, pp. 111-122, vol. 43.
Baldeweg et al., "Mismatch negativity potentials and cognitive impairment in schizophrenia", Schizophrenia Research, 2004, pp. 203-217, vol. 69.
Barak, "Modeling cholinergic aspects of schizophrenia: Focus on the antimuscarinic syndrome", Behavioural Brain Research, 2009, pp. 335-351, vol. 204.
Bartos et al., "Synaptic mechanisms of synchronized gamma oscillations in inhibitory interneuron networks", Nature Reviews Neuroscience, 2007, pp. 45-56, vol. 8.
Bechter et al., "Cerebrospinal fluid analysis in affective and schizophrenic spectrum disorders: Identification of subgroups with immune responses and blood-CSF barrier dysfunction", Journal of Psychiatric Research, 2010, pp. 321-330, vol. 44.
Begleiter et al., "The P300 Component of the Event-Related Brain Potential in Psychiatric Patients", Evoked Potentials, 1986, pp. 529-535.
Begum et al., "Long Term Effect of Herbal Drug Withania somnifera on Adjuvant Induced Arthritis in Rats", Indian Journal of Experimental Biology, 1988, pp. 877-882, vol. 26.
Behrens et al., "Ketamine-Induced Loss of Phenotype of Fast-Spiking Interneurons Is Mediated by NADPH-Oxidase", Science, 2007, pp. 1645-1647, vol. 318.
Behrens et al., "Interleukin-6 Mediates the Increase in NADPH-Oxidase in the Ketamine Model of Schizophrenia", J Neurosci., 2008, pp. 13957-13966, vol. 28:51.
Berk et al., "N-Acetyl Cysteine as a Glutathione Precursor for Schizophrenia—A Double-Blind, Randomized, Placebo-Controlled Trial", Biol Psychiatry, 2008, pp. 361-368, vol. 64.
Bhattarai et al., "Potentiation of NMDA Receptors by Withania somnifera on Hippocampal CA1 Pyramidal Neurons", The American Journal of Chinese Medicine, 2013, pp. 503-513, vol. 41:3.
Bhattarai et al., "Phasic and tonic type A γ-Aminobutryic acid receport mediated effect of Withania somnifera on mice hippocampal CA1 pyramidal Neurons", Journal of Ayurveda & Integrative Medicine, 2014, pp. 216-222, vol. 5:4.

(56) References Cited

OTHER PUBLICATIONS

Brenhouse et al., "Nonsteroidal Anti-Inflammatory Treatment Prevents Delayed Effects of Early Life Stress in Rats", Biol Psychiatry, 2011, pp. 434-440, vol. 70:5.
Buchanan et al., "The Cognitive and Negative Symptoms in Schizophrenia Trial (CONSIST): The Efficacy of Glutamatergic Agents for Negative Symptoms and Cognitive Impairments", Am J Psychiatry, 2007, pp. 1593-1602, vol. 164.
Buelna-Chontal et al., "Redox activiation of Nrf2 & NF-kB: A double end sword?", Cellular Signaling, 2013, pp. 2548-2557, vol. 25.
Candelario et al., "Direct evidence for GABAergic activity of Withania somnifera on mammalian ionotropic GABAa and GABAp receptors", Journal of Ethnopharmacology, 2015, pp. 264-272, vol. 171.
Carlsson et al., "Interactions between glutamatergic and monoaminergic systems within the basal ganglia—implications for schizophrenia and Parkinson's disease", Cell Press, 1990, pp. 272-274, vol. 13:7, Abstract only.
Carmeli et al., "Glutathione Precursor N-Acetyl-Cysteine Modulates EEG Synchronization in Schizophrenia Patients: A Double-Blind, Randomized, Placebo-Controlled Trial", PLOS One, 2012, pp. 1-9, vol. 7:2.
Catts et al., "Brain Potential Evidence for an Auditory Sensory Memory Deficit in Schizophrenia", Am J Psychiatry, 1995, pp. 213-219, vol. 152.
Chengappa et al., "Randomized Placebo-Controlled Adjunctive Study of an Extract of Withania somnifera for Cognitive Dysfunction in Bipolar Disorder", J Clin Psychiatry, 2013, pp. 1076-1083, vol. 74:11.
Choudhary et al., "Withanolides, a new class of natural cholinesterase inhibitors with calcium antagonistic properties", Biochemical and Biophysical Research Communications, 2005, pp. 276-287, vol. 334.
Cohen, "Quantitative Methods in Psychology: A Power Primer", Psychological Bulletin, 1992, pp. 155-159, vol. 112:1.
Cohen et al., "Perceived Stress Scale (PSS)", Handbook of Psychiatry Measures, 2nd Edition, American Psychiatric Publishing, Inc., Washington, D.C., 2000, pp. 204-206.
Cooley et al., "Naturopathic Care of Anxiety: A Randomized Controlled Trial ISRCTN78958974", PLOS One, 2009, pp. 1-10, vol. 4:8.
Cotgreave, "N-acetylcysteine: pharmacological considerations and experimental and clinical applications.", Adv Pharmacol, 1997, pp. 205-227, vol. 38, Abstract only.
Coyle et al., "Glutamatergic Synaptic Dysregulation in Schizophrenia: Therapeutic Implications", Handb Exp Pharmacol, 2012, pp. 267-295, vol. 213.
Cunha et al., "Investigation of serum high-sensitive C-reactive protein levels across all mood states in bipolar disorder", Eur Arch Psychiatry Clin Neurosci, 2008, pp. 300-304, vol. 258.
Dar et al., "Pharmacologic overview of *Withania somnifera*, the Indian Ginseng", Cell. Mol. Life Sci., 2015, pp. 4445-4460, vol. 72.
Dar et al., "Withanone, an Active Constituent from Withania somnifera, Affords Protection Against NMDA-Induced Excitotoxicity in Neuron-Like Cells", Mol Neurobiol, 2017, pp. 5061-5073, vol. 54.
Das et al., "Increased arachidonic acid induced platelet chemiluminescence indicates cyclooxygenase overactivity in schizophrenic subjects", Prostaglandins, Leukotrienes and Essential Fatty Acids, 1998, pp. 165-168, vol. 58:3.
Davis et al., "Psychopharmacology of the negative symptoms: Current status and prospects for progress", European Neuropsychopharmacology, 2014, pp. 788-799, vol. 24.
Dickerson et al., "C-reactive protein is associated with the severity of cognitive impairment but not of psychiatric symptoms in individuals with schizophrenia", Schizophrenia Research, 2007, pp. 261-265, vol. 93.
Doorduin et al., "Neuroinflammation in Schizophrenia-Related Psychosis: A PET Study", J Nucl Med, 2009, pp. 1801-1807, vol. 50.

Duncan, "Event-Related Brain Potentials: A Window on Information Processing in Schizophrenia", Schizophrenia Bulletin, 1988, pp. 199-203, vol. 14:2.
Erhardt et al., "Kynurenic acid levels are elevated in the cerebrospinal fluid of patients with schizophrenia", Neuroscience Letters, 2001, pp. 96-98, vol. 313.
Fan et al., "Elevated serum levels of C-reactive protein are associated with more severe psychopathology in a subgroup of patients with schizophrenia", Psychiatry Research, 2007, pp. 267-271, vol. 149.
Fillman et al., "Increased inflammatory markers identified in the dorsolateral prefrontal cortex of individuals with schizophrenia", Molecular Psychiatry, 2013, pp. 206-214, vol. 18.
Ford et al., "ERPs in Schizophrenia: Effects of Antipsychotic Medication", Biol Psychiatry, 1994, pp. 153-170, vol. 36.
Freedman et al., "Evidence in Postmortem Brain Tissue for Decreased Numbers of Hippocampal Nicotinic Receptors in Schizophrenia", Biol Psychiatry, 1995, pp. 22-33, vol. 38.
Gandal et al., "Gamma synchrony: towards a translational biomarker for the treatment resistant symptoms of schizophrenia", Neuropharmacology, 2012, pp. 1504-1518, vol. 62:3.
Ganguli et al., "Mitogen-Stimulated Interleukin-2 Production in Never-Medicated, First-Episode Schizophrenic Patients", Arch Gen Psychiatry, 1995, pp. 668-672, vol. 52.
Garcia-Bueno et al., "Pro-/ Anti-inflammatory Dysregulation in Patients With First Episode of Psychosis: Toward an Integrative Inflammatory Hypothesis of Schizophrenia", Schizophrenia Bulletin, 2014, pp. 376-387, vol. 40:2.
Gonzalez-Burgos et al., "NMDA Receptor Hypofunction, Parvalbumin-Positive Neurons, and Cortical Gamma Oscillations in Schizophrenia", Schizophrenia Bulletin, 2012, pp. 950-957, vol. 38:5.
Grace, "Phasic Versus Tonic Dopamine Release and the Modulation of Dopamine System Responsivity: A Hypothesis for the Etiology of Schizophrenia", Neuroscience, 1991, pp. 1-24, vol. 41:1.
Grotta et al., "Safety and Tolerability of the Glutamate Antagonist CGS 19755 (Selfotel) in Patients With Acute Ischemic Stroke: Results of a Phase IIa Randomized Trial", Stroke, 1995, pp. 602-605, vol. 26.
Grover et al., "Computational Evidence to Inhibition of Human Acetyl Cholinesterase by Withanolide A for Alzheimer Treatment", Journal of Biomolecular Structure & Dynamics, 2012, pp. 651-662, vol. 29:4.
Gupta et al., "Aqueous extract from the Withania somnifera leaves as a potential anti-neuroinflammatory agent: a mechanistic study", Journal of Neuroinflammation, 2016, pp. 1-17, vol. 13:193.
Hilmas et al., "The Brain Metabolite Kynurenic Acid Inhibits α7 Nicotinic Receptor Activity and Increases Non-α7 Nicotinic Receptor Expression: Physiopathological Implications", The Journal of Neuroscience, 2001, pp. 7463-7473, vol. 21:19.
Hoftman et al., "Chapter 5: Neurobiology of Schizophrenia", Schizophrenia and Related Disorders, pp. 143-184.
Javitt et al., "Recent Advances in the Phencyclidine Model of Schizophrenia", Am J Psychiatry, 1991, pp. 1301-1308, vol. 148.
Javitt et al., "Role of cortical N-methyl-D-aspartate receptors in auditory sensory memory and mismatch negativity generation: Implications for schizophrenia", Proc. Natl. Acad. Sci., 1996, pp. 11962-11967, vol. 93.
Javitt et al., "Impaired mismatch negativity (MMN) generation in schizophrenia as a function of stimulus deviance, probability, and interstimulus/interdeviant interval", Electroencephalography and clinical Neurophysiology, 1998, pp. 143-153, vol. 108.
Jayaprakasam et al., "Growth inhibition of human tumor cell lines by withanolides from Withania somnifera leaves", Life Sciences, 2003, pp. 125-132, vol. 74.
Kaiya et al., "Elevated plasma prostaglandin E2 levels in schizophrenia", J Neural Transm, 1989, pp. 39-46, vol. 77.
Kantrowitz et al., "Improvement in mismatch negativity generation during D-serine treatment in schizophrenia: Correlation with symptoms", Schizophrenia Research, 2017, pp. 1-10.
Kasai et al., "Do high or low doses of anxiolytics and hypnotics affect mismatch negativity in schizophrenic subjects? An EEG and MEG study", Clinical Neurophysiology, 2002, pp. 141-150, vol. 113.

(56) References Cited

OTHER PUBLICATIONS

Kataria et al., "Water Extract from the Leaves of Withania somnifera Protect RA Differentiated C6 and IMR-32 Cells against Glutamate-Induced Excitotoxicity", PLOS One, 2012, pp. 1-13, vol. 7:5.
Kawakubo et al., "Phonetic mismatch negativity predicts verbal memory deficits in schizophrenia", NeuroReport, 2006, pp. 1043-1046, vol. 17.
Kawakubo et al., "Phonetic mismatch negativity predicts social skills acquisition in schizophrenia", Psychiatry Research, 2007, pp. 261-265, vol. 152.
Kay et al., "The Positive and Negative Syndrome Scale (PANSS) for Schizophrenia", Schizophrenia Bulletin, 1987, pp. 261-276, vol. 13:2.
Khan et al., "Augmentation and proliferation of T lymphocytes and Th-1 cytokines by Withania somnifera in stressed mice", International Immunopharmacology, 2006, pp. 1394-1403, vol. 6.
Kim et al., "Low cerebrospinal fluid glutamate in schizophrenic patients and a new hypothesis on schizophrenia", Neuroscience Letters, 1980, pp. 379-382, vol. 20:3, Abstract only.
Kim et al., "NF-kB and Cytokines in Pancreatic Acinar Cells", J Korean Med Sci, 2000, pp. s53-s54, vol. 15.
Konar et al., "Protective Role of Ashwagandha Leaf Extract and Its Component Withanone on Scopolamine-Induced Changes in the Brain and Brain-Derived Cells", PLOS One, 2011, pp. 1-12, vol. 6:11.
Korostenskaja et al., "Effects of olanzapine on auditory P300 and mismatch negativity (MMN) in schizophrenia spectrum disorders", Progress in Neuro-Psychopharmacology & Biological Psychiatry, 2005, pp. 543-548, vol. 29.
Kour et al., "Restoration of stress-induced altered T cell function and corresponding cytokines patterns by Withanolide A", International Immunopharmacology, 2009, pp. 1137-1144, vol. 9.
Krystal et al., "Subanesthetic Effects of the Noncompetitive NMDA Antagonist, Ketamine, in Humans", Arch Gen Psychiatry, 1994, pp. 199-214, vol. 51.
Krystal et al., "NMDA receptor antagonist effects, cortical glutamatergic function, and schizophrenia: toward a paradigm shift in medication development", Psychopharmacology, 2003, pp. 215-233, vol. 169.
Kumar et al., "Exploring neuroprotective potential of Withania somnifera phytochemicals by inhibition of GluN2B-containing NMDA receptors: An in silico study", Medical Hypotheses, 2016, pp. 35-43, vol. 92.
Kwon et al., "Gamma Frequency-Range Abnormalities to Auditory Stimulation in Schizophrenia", Arch Gen Psychiatry, 1999, pp. 1001-1005, vol. 56.
Laan et al., "Adjuvant Aspirin Therapy Reduces Symptoms of Schizophrenia Spectrum Disorders: Results From a Randomized, Double-Blind, Placebo-Controlled Trial", J Clin Psychiatry, 2010, pp. 520-527, vol. 71:5.
Laughren et al., "Food and Drug Administration Perspective on Negative Symptoms in Schizophrenia as a Target for a Drug Treatment Claim", Schizophrenia Bulletin, 2006, pp. 220-222, vol. 32:2.
Laughren et al., "Food and Drug Administration Commentary on Methodological Issues in Negative Symptom Trials", Schizophrenia Bulletin, 2011, pp. 255-256, vol. 37:2.
Lavoie et al., "Glutathione Precursor, N-Acetyl-Cysteine, Improves Mismatch Negativity in Schizophrenia Patients", Neuropsychopharmacology, 2008, pp. 2187-2199, vol. 33.
Leucht et al., "Dose Equivalents for Antipsychotic Drugs: The DDD Method", Schizophrenia Bulletin, 2016, pp. S90-S94, vol. 42:1.
Lewis et al., "Subunit-Selective Modulation of GABA Type A Receptor Neurotransmission and Cognition in Schizophrenia", Am J Psychiatry, 2008, pp. 1585-1593, vol. 165:12.
Lewis et al., "Cortical Parvalbumin Interneurons and Cognitive Dysfunction in Schizophrenia", Trends Neurosci., 2012, pp. 57-67, vol. 35:1.
Leza et al., "Inflammation in schizophrenia: A question of balance", Neuroscience and Biobehavioral Reviews, 2015, pp. 612-626, vol. 55.
Light et al., "Mismatch Negativity Deficits Are Associated With Poor Functioning in Schizophrenia Patients", Arch Gen Psychiatry, 2005, pp. 127-136, vol. 62.
Light et al., "Stability of Mismatch Negativity Deficits and Their Relationship to Functional Impairments in Chronic Schizophrenia", Am J Psychiatry, 2005, pp. 1741-1743, vol. 162.
Light et al., "Gamma Band Oscillations Reveal Neural Network Cortical Coherence Dysfunction in Schizophrenia Patients", Biol Psychiatry, 2006, pp. 1231-1240, vol. 60.
Lisman et al., "Circuit-based framework for understanding neurotransmitter and risk gene interactions in schizophrenia", Trends Neurosci, 2008, pp. 234-242, vol. 31:5.
Maeda et al., "Amplitude and Area of the Auditory P300 Recorded with Eyes Open Reflect Remission of Schizophrenia", Biol Psychiatry, 1996, pp. 743-746, vol. 39.
Malik et al., "A standardized root extract of Withania somnifera and its major constituent withanolide-A elicit humoral and cell-mediated immune responses by up regulation of Th1-dominant polarization in BALB/c mice", Life Sciences, 2007, pp. 1525-1538, vol. 80.
Meyer et al., "Inflammatory Markers in Schizophrenia: Comparing Antipsychotic Effects in Phase 1 of the CATIE Schizophrenia Trial", Biol Psychiatry, 2009, pp. 1013-1022, vol. 66:11.
Meyer et al., "Inflammatory processes in schizophrenia: A promising neuroimmunological target for the treatment of negative/cognitive symptoms and beyond", Pharmacology & Therapeutics, 2011, pp. 96-110, vol. 132.
Michie et al., "The neurobiology of MMN and implications for schizophrenia", Biological Psychology, 2016, pp. 90-97, vol. 116.
Mikolai et al., "In Vivo Effects of Ashwagandha (*Withania somnifera*) Extract on the Activation of Lymphocytes", The Journal of Alternative and Complementary Medicine, 2009, pp. 423-430, vol. 15:4.
Muller et al., "C-Reactive Protein Levels in Schizophrenia: A Review and Meta-Analysis", Clinical Schizophrenia & Related Psychoses, 2014, pp. 223-230.
Miller et al., "Meta-Analysis of Cytokine Alterations in Schizophrenia: Clinical Status and Antipsychotic Effects", Biol Psychiatry, 2011, pp. 663-671, vol. 70:7.
Mittleman et al., "Cerebrospinal Fluid Cytokines in Pediatric Neuropsychiatric Disease", The Journal of Immunology, 1997, pp. 2994-2999, vol. 159.
Clinical Trials Registry No. NCT-1793935, Withania Somnifera: an Immunomodulator and Anti-inflammatory Agent for Schizophrenia; available at https://www.clinicaltrials.gov/ct2/show/record/NCT01793935?cond=Schizophrenia&id=NCT01793935&draw=2&rank=1&view=record; Feb. 18, 2013.
Kumar et al., "Anxiolytic Profile of a Polyherbal Drug Mentat," Int. J. Pharm. Med. & Bio. Sc., Oct. 2013, pp. 21-27, vol. 2, No. 4.
Powell et al., "Schizophrenia-Relevant Behavioral Testing in Rodent Models: A Uniquely Human Disorder?," Biol Psychiatry, Jun. 15, 2006, pp. 1198-1207, vol. 59(12).
Tohda et al., "Scientific basis for the anti-dementia drugs of constituents from Ashwagandha (*Withania somnifera*)," J. Trad. Med., 2005, pp. 176-182, vol. 22 (Suppl. 1).

* cited by examiner

PANSS and PSS Rating Scale Scores

| | Sensoril | | | Placebo | | | Statistics: Differences between Delta Means |
|---|---|---|---|---|---|---|---|
| | Baseline Mean (SD) n = 33 | 12 Weeks Mean (SD) n = 33 | Delta Mean (SD) n = 33 | Baseline Mean (SD) n = 33 | 12 Weeks Mean (SD) n = 33 | Delta Mean (SD) n = 33 | t-test, df, p |
| PANSS Positive | 19.58 (3.34) | 14.39 (3.94) | 5.18 (2.59) | 18.97 (2.57) | 15.33 (4.75) | 3.64 (3.73) | 1.95, 64, 0.055 |
| PANSS Negative | 16.52 (4.52) | 12.97 (4.46) | 3.55 (2.72) | 17.27 (5.25) | 15.88 (5.75) | 1.39 (2.45) | 3.38, 64, 0.001 |
| PANSS General | 33.79 (5.04) | 26.55 (4.99) | 7.24 (6.09) | 33.24 (5.27) | 30.27 (7.45) | 2.97 (5.13) | 3.08, 64, 0.003 |
| PANSS Total | 69.88 (8.00) | 53.91 (11.48) | 15.97 (9.76) | 69.48 (8.45) | 61.48 (14.89) | 8.00 (9.41) | 3.38, 64, 0.001 |
| PSS Scores | 20.48 (7.27) | 14.67 (5.87) | 5.82 (5.60) | 20.55 (6.68) | 18.09 (6.64) | 2.45 (6.00) | 2.36, 64, 0.022 |

PANSS = Positive and Negative Syndrome Scale, PSS = Perceived Stress Scale, SD = standard deviation PANSS and PSS Scores ≥ 20% Improvement Versus Not Between Treatment Groups

| | Sensoril n = 33 N (%) | Placebo n = 33 N (%) | Statistics $\chi^2$, df, p |
|---|---|---|---|
| PANSS Positive | 25 (76%) | 19 (58%) | 2.46, 1, ns |
| PANSS Negative | 18 (55%) | 6 (18%) | 9.43, 1, 0.002 |
| PANSS General | 19 (58%) | 9 (27%) | 6.20, 1, 0.013 |
| PANSS Total | 20 (61%) | 10 (30%) | 6.11, 1, 0.013 |
| PSS Total | 25 (76%) | 15 (45%) | 6.35, 1, 0.012 |

PANSS = Positive and Negative Syndrome Scale, PSS = Perceived Stress Scale, ns = not statistically significant, Sensoril = standardized extract of Withania somnifera

*Fig. 2*

| S100b levels from baseline to end to Rx | | | | | | | |
|---|---|---|---|---|---|---|---|
| | WSE | | | Placebo | | | Differences Between Delta Means |
| | Baseline Mean (SD) n = 31 | 12 weeks Mean (SD) n = 31 | Delta Mean (SD) n = 31 | Baseline Mean (SD) n = 32 | 12 weeks Mean (SD) n = 32 | Delta Mean (SD) n = 32 | Mann-Whitney Test, U, P |
| S100b pg/ml | 39.36 (89.92) | 26.38 (79.44) | 12.98 (112.89) (decrease) | 34.95 (56.12) | 62.49 (173.92) | 27.54 (145.41) (increase) | 469.50, p = 0.72 |
| hsCRP levels from baseline to end of Rx | | | | | | | |
| | WSE | | | Placebo | | | Differences Between Delta Means |
| | Baseline Mean (SD) n = 30 | 12 weeks Mean (SD) n = 30 | Delta Mean (SD) n = 30 | Baseline Mean (SD) n = 30 | 12 weeks Mean (SD) n = 30 | Delta Mean (SD) n = 30 | Mann-Whitney Test, U, P |
| hsCRP mg/L | 5.57 (8.57) | 4.38 (5.05) | 1.08 (6.98) (decrease) | 6.27 (6.90) | 7.82 (8.25) | 1.55 (5.58) (increase) | 372.50, p = 0.25 |
| IL6 levels from baseline to end of Rx | | | | | | | |
| | WSE | | | Placebo | | | Differences Between Delta Means |
| | Baseline Mean (SD) n = 30 | 12 weeks Mean (SD) n = 30 | Delta Mean (SD) n = 30 | Baseline Mean (SD) n = 31 | 12 weeks Mean (SD) n = 31 | Delta Mean (SD) n = 31 | Mann-Whitney Test, U, P |
| IL6 pg/mL | 3.37 (2.53) | 3.40 (2.51) | 0.03 (1.87) (increase) | 4.29 (3.34) | 3.87 (2.57) | 0.42 (3.50) (decrease) | 458.0, p = 0.92 |

WSE: Withania somnifera extract, hsCRP, high sensitivity C reactive protein, SD = standard deviation

*Fig. 7*

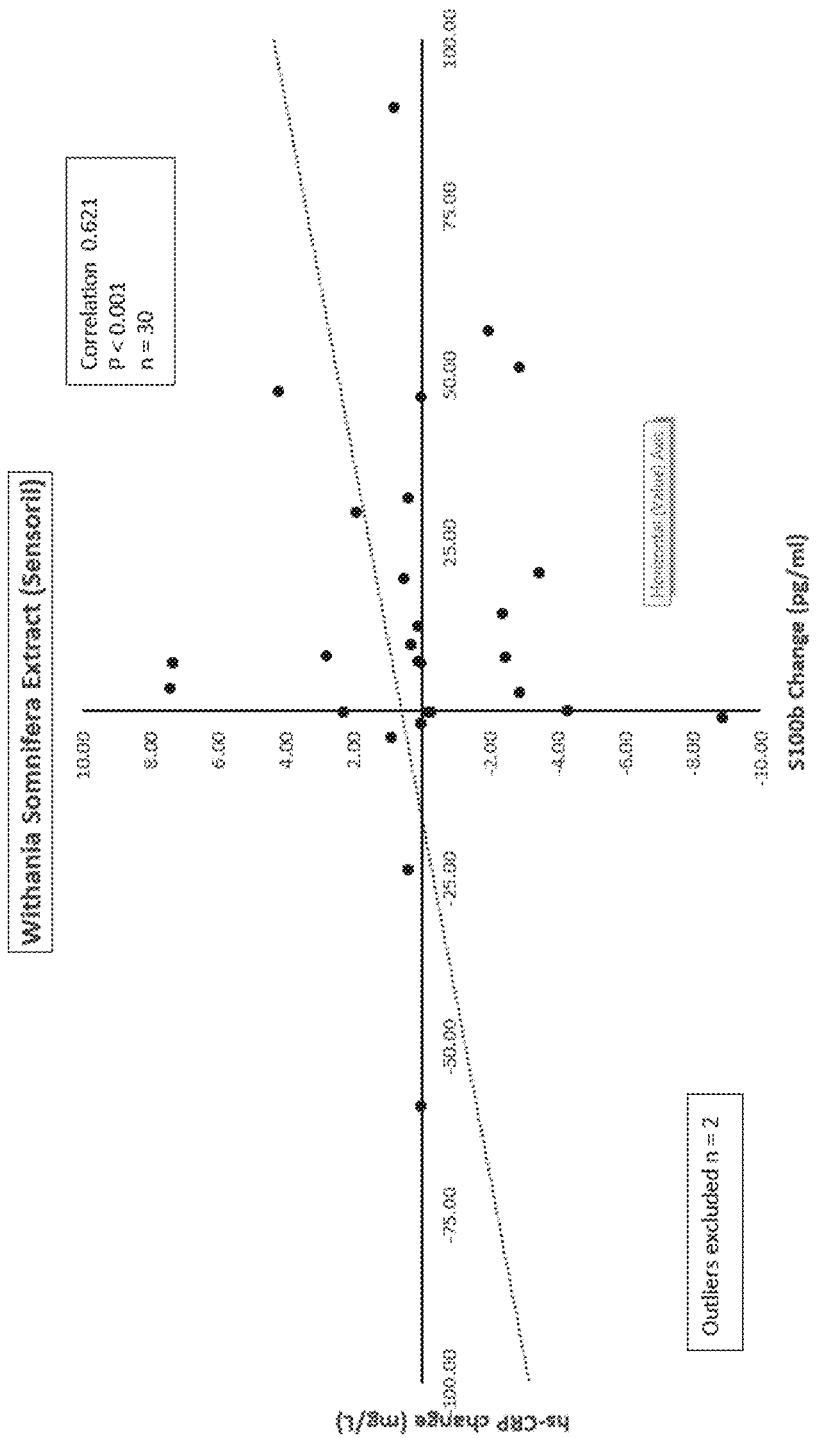

Changes in Weight, Body Mass Index and Vitals

| | Sensoril | | | Placebo | | | Between Groups Statistics |
|---|---|---|---|---|---|---|---|
| | Baseline Mean (SD) N = 33 | End of Rx Mean (SD) N = 33 | Delta Mean (SD) N = 33 | Baseline Mean (SD) N = 33 | End of Rx Mean (SD) N = 33 | Delta Mean (SD) N = 33 | t-test, df, p. |
| Body Weight (lbs) | 194.61 (49.57) | 197.00 (51.94) | 2.40 (7.04) | 191.33 (41.29) | 193.06 (41.33) | 1.73 (5.66) | 0.42, 64, p = 0.67 |
| Body Mass Index | 30.00 (7.56) | 30.33 (8.04) | 0.33 (1.08) | 30.36 (6.35) | 30.56 (6.24) | 0.20 (0.91) | 0.53, 64, p = 0.60 |
| Blood Pressure | | | | | | | |
| Systolic (mm/Hg) | 124.67 (10.53) | 123.36 (9.30) | -1.31 (8.36) | 123.42 (15.32) | 118.39 (23.19) | -5.03 (25.24) | 0.81, 64, p = 0.42 |
| Diastolic (mm/Hg) | 79.15 (7.95) | 79.06 (7.31) | -0.09 (6.27) | 76.52 (11.52) | 75.55 (13.21) | -0.97 (13.60) | 0.34, 64, p = 0.74 |
| Pulse (beats/min) | 76.18 (13.38) | 75.42 (14.64) | -0.76 (10.59) | 74.91 (11.75) | 76.42 (9.56) | 1.51 (8.53) | 0.96, 64, p = 0.34 |
| Temperature (°F) | 97.38 (0.57) | 97.37 (0.73) | -0.01 (0.62) | 97.36 (0.72) | 97.31 (0.46) | 0.05 (0.51) | 0.53, 63, p = 0.60 |

SD = standard deviation, Rx = treatment, df = degrees of freedom, Sensoril = standardized extract of Withania somnifera

*Fig. 9*

METHODS AND COMPOSITIONS FOR TREATING SCHIZOPHRENIA AND SCHIZOAFFECTIVE DISORDERS

CROSS REFERENCE TO RELATED APPLICATIONS

This application is the United States national phase of International Application No. PCT/US2017/050234 filed Sep. 6, 2017, and claims benefit of U.S. Provisional Patent Application No. 62/463,836 filed Feb. 27, 2017, each of which is incorporated herein by reference in its entirety.

BACKGROUND OF THE INVENTION

Methods and compositions are provided for treatment of psychotic conditions, such as schizophrenia and schizoaffective disorder.

Current treatment approaches for patients who take medications but experience breakthrough symptoms in schizophrenia or schizoaffective disorder include adjustment of preexisting medications (i.e., dosage) or switching to another medication or adding other anti-psychotic medications. Each of these approaches help to curb what are called positive symptoms of schizophrenia (e.g., hallucinations, delusions, thought disorganization etc.), but usually do not help much if at all with negative symptoms (e.g., loss of motivation, loss of energy, slowed thinking and slowed speech production, slowed movements, no interest in getting things done, etc.) and do not help significantly with general symptoms (e.g., depression anxiety, fatigue, etc.).

Recent elaborations of the immune-inflammatory dysregulation theory in schizophrenia have opened new treatment vistas for persons with schizophrenia. An imbalance of pro and anti-inflammatory cytokines and elevated levels of inflammatory markers (e.g., C-reactive protein, S100B and prostaglandin E2) have been reported in subgroups of patients with schizophrenia, especially those experiencing an exacerbation of symptoms. These immune-inflammatory alterations are known to impact dopaminergic, glutamatergic and cholinergic neurotransmission, which in turn are linked to the positive, negative and cognitive symptoms noted in schizophrenia. Reviews have concluded that antipsychotic medications do not appear to mitigate immune-inflammatory disturbances. A case has been made for adjunctive treatment of symptoms of schizophrenia using anti-inflammatory drugs, e.g., Cox inhibitors, since these medications shift the immune responsivity from predominantly type-2 to type-1 and inhibit prostaglandin E2 (PGE2) synthesis. A review of 8 randomized controlled trials, including unpublished studies, mostly involving patients experiencing symptom exacerbations indicated that adjunctive Cox-2 inhibitors (celecoxib, six studies) or non-selective Cox-1/Cox-2 inhibitors (aspirin, two studies) showed a small treatment effect for positive symptoms of schizophrenia and trend level significance for total psychopathology but no effects for negative symptoms. Concerns about cardiac safety and bleeding risks associated with non-steroidal anti-inflammatory agents (NSAIDS) call for alternative anti-inflammatory agents to be tested for symptom exacerbations in schizophrenia.

Mismatch Negativity (MMN) is an event-related potential (ERP) captured in an electroencephalogram (EEG) in humans, but also in other animals, typically in response to a rare deviant sound in a series of standard repetitive auditory sounds. The detection of the deviant sound generates the MMN. The deviant sound can be different in pitch, duration, frequency or intensity from the standard sound. Alteration in mismatch negativity (MMN) is among the most highly replicated (>200 studies) abnormalities reported in schizophrenia. In long standing schizophrenia, the amplitude of MMN is reduced for a frequency or duration change. In a meta-analysis, Umbricht and Krljes (Mismatch negativity in schizophrenia: A meta-analyses. Schizophrenia Research 2005, 76:1-25) estimated the overall effect size for the MMN abnormality in schizophrenia is 0.99 which is considered large. MMN abnormalities are highly correlated with impaired day to day and executive functioning as well as in the acquisition of social skills in people with schizophrenia. Moreover, MMN abnormalities also correlate with negative symptoms which also impair day to day functioning in persons with schizophrenia.

Standard anti-psychotic drugs used to treat mainly the positive symptoms (examples: hallucinations, delusions, disorganized thinking and behavior) do not improve MMN. Marketed anti-psychotic drugs mostly are dopamine receptor antagonists and they do not improve the MMN abnormality in schizophrenia which is more closely linked to another neurotransmitter system, i.e. N-methyl-D-aspartate glutamate receptors (NMDAR). Moreover, these anti-psychotic drugs do not improve negative symptoms (examples include: emotional blunting and minimal facial expressiveness, poverty of speech in response to questions from others and minimal spontaneous speech, poorly motivated to engage in day to day activities, and show low energy and slowed thought processes and come across as socially disengaged from others). Therefore, there is a significant unmet need in improving the neurophysiological abnormalities (e.g. MMN) and negative symptoms in persons with schizophrenia or schizoaffective disorder.

Unlike MMN, elicited passively and automatically by auditory cortex, the P300 event-related potential is elicited during the active detection of rare target stimuli. It too is severely impaired in schizophrenia even at first episode. Widespread scalp-recorded amplitude reduction of the auditory P300 event-related potential in schizophrenia is well documented and robust. Furthermore, auditory P300 reduction in schizophrenia appears to show trait characteristics, being unimproved with resolution of overt psychotic symptomotology; even when variation with scores on the Brief Psychosis Rating Scale are reported, P300 amplitudes remain smaller in schizophrenic than in control subjects.

Another ERP that is reduced in schizophrenia is the gammaband auditory steady state response (ASSR). When short clicks (1 msec duration) are played at 40 Hz, the brain responds by oscillating at the stimulation frequency (40 Hz) the so-called gammaband. The gammaband ASSR is reduced in long-term schizophrenia, and at first episode, and reductions in the gammaband ASSR, related to NMDA and GABA imbalance, are associated with impaired cognitive functioning.

There is a need for compositions, active agents and methods of improving negative symptoms, mismatch negativity, P300, and gammaband abnormalities in schizophrenia and schizoaffective disorders.

SUMMARY

A method of treating a psychiatric disorder for which an antipsychotic drug is administered in a patient is provided according to one aspect of the invention. The method comprises administering to the patient a *Withania somnifera* active agent in combination with an antipsychotic active agent in amounts effective to treat the psychiatric disorder.

According to another aspect, a pharmaceutical dosage form, or composition, is provided for use in treatment of a psychiatric disorder for which an antipsychotic drug is administered. The composition comprises comprising an antipsychotic agent and a *W. somnifera* active agent in amounts effective to treat the psychiatric disorder, such as a psychotic disorder, such as schizophrenia or schizoaffective disorder, and optionally one or more negative symptoms of the psychiatric disorder.

According to a further aspect, a *W. somnifera* active agent is provided for use in the treatment of a negative symptom of a psychiatric disorder, e.g. for which an antipsychotic drug is administered.

In the various aspects, the psychiatric disorder may be a psychotic disorder, such as schizophrenia or a schizoaffective disorder, for example, selected from the group consisting of: schizophrenia; Schizophrenia, Paranoid Type; Schizophrenia, Disorganized Type; Schizophrenia, Undifferentiated Type; Schizophrenia, Residual Type; Schizoaffective Disorder; Schizophreniform Disorder; Delusional Disorder; Brief Psychotic Disorder; Other specified Schizophrenia Spectrum and other Psychotic Disorder; Unspecified Schizophrenia Spectrum, and other Psychotic Disorder.

In the various aspects, a negative symptom of the psychiatric disorder is improved in the patient after administration of the *W. somnifera* active agent to the patient; stress symptoms, depression, anxiety, and/or excitation symptoms of the psychiatric disorder is improved in the patient after administration of the *W. somnifera* active agent to the patient and/or a sensory or cognitive symptom of the psychiatric disorder, such as an electroencephalogram response to an auditory stimulus, for example a mismatch negativity abnormality, a P300 event-related potential, or a gammaband auditory steady state response, is improved in the patient after administration of the *W. somnifera* active agent to the patient.

BRIEF DESCRIPTION OF THE DRAWING(S)

FIGS. 1A-1F provide structures of various *W. somnifera* active agents.

FIG. 2 is a table showing PANSS (Positive and Negative Syndrome Scale, Kay et al, 1987) and PSS Rating Scale (Perceived Stress Scale, Cohen et al, 2000) Scores.

FIGS. 3A-3D provide graphs showing changes in PANSS Scores in Patients receiving *W. somnifera* Extract or Placebo; Negative Symptoms—Visit 4 p=0.025, Visit 5 p=0.001, Visit 6 p<0.001; General Symptoms—Visit 4 p=0.007, Visit 5 p<0.001, Visit 6 p<0.001; Total Symptoms—Visit 4 p=0.038, Visit 5 p<0.001, Visit 6 p<0.001.

FIG. 7 is a table providing, from baseline to end of Rx, S100b, hsCRP, and IL-6 levels for patients in Example 1.

FIGS. 8A and 8B are graphs showing correlation between hsCRP and S100B for patients receiving *W. somnifera* Extract or placebo, respectively, for patients in Example 1.

FIG. 9 is a table providing weight, Body Mass Index (BMI) and vital signs for patients in Example 1.

Figure 10A:
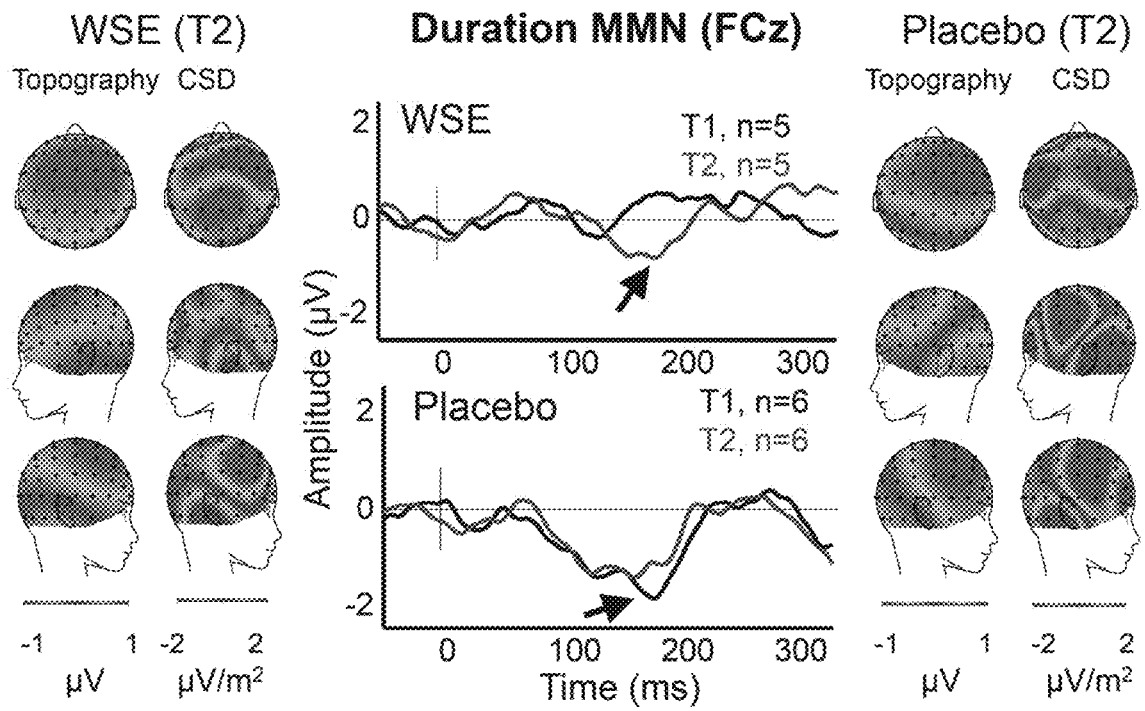
Figure 10B:
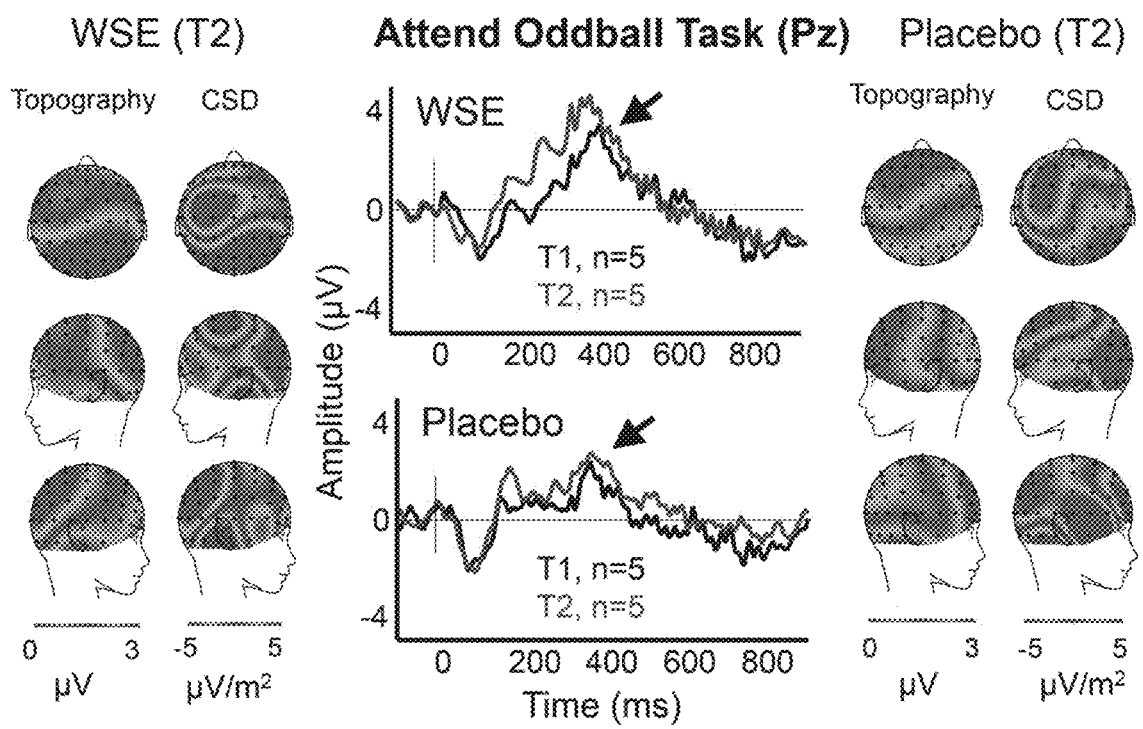
Figure 10C:
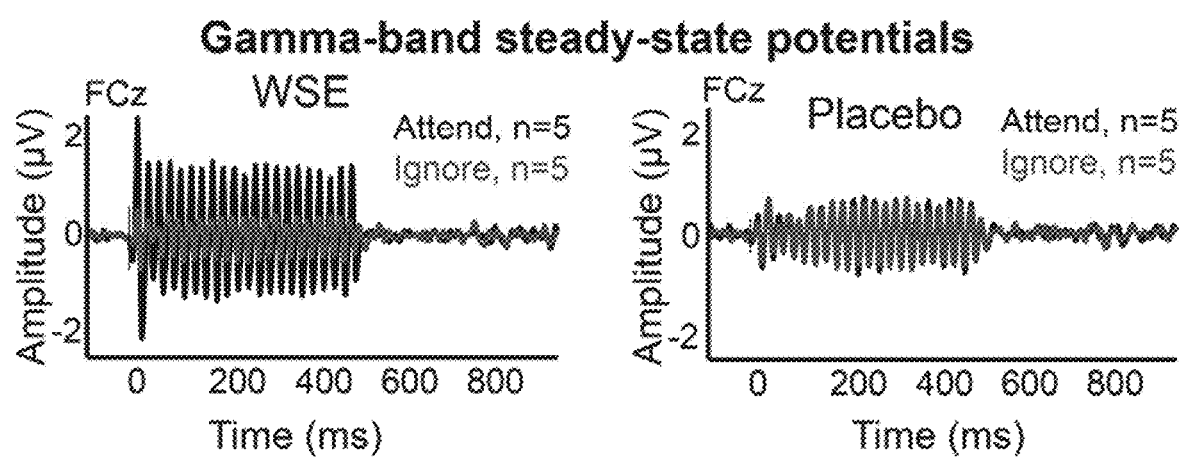

FIGS. 10A-10C providing MMN, P300, and gamma-band data, respectively, for patients receiving *W. somnifera* Extract or placebo for patients in Example 2.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

A "patient" is a human being and does not imply a doctor-patient relationship. "Treatment" of a patient refers to improvement of one or more clinically-relevant symptoms of a stated disorder, disease, or condition. In the context of schizophrenia, schizoaffective disorder, and other disorders listed above, there are symptoms that are positive, negative, or general. Positive symptoms include: hallucinations, delusions, bizarre thoughts, disorganized thoughts, etc. Often, positive symptoms respond to available anti-psychotic drugs. Negative symptoms include: diminished facial emotionality (facial expressions are wooden and fixed and often without a smile even when it is appropriate), lack of interest and detachment from family, relatives, friends, or fellow patients etc., uncommunicative or minimally communicative and withdrawn, neglect of personal grooming and hygiene, distant and apathetic towards family, friends, clinical staff during conversations, little to no energy, no motivation, difficulty with abstract thinking, can be very concrete in response to the meanings of proverbs or common day to day categorizations, barely speaks or even if he or she does, minimal output and no normal elaboration of sentences, rigid thinking and repetition of ideas, slowed down thinking etc. In contrast to positive symptoms, negative symptoms do not respond to available antipsychotic drugs. General symptoms include: somatic preoccupation with several bodily symptoms, anxiety, depression, guilt feelings, tension, overall slowing down of speech and activity inadequately cooperative, poor attention and concentration, not fully oriented, exhibiting poor judgement and insight, poor impulse control, social avoidance, etc. In various aspects, the PANSS scale, and subscales thereof, or the Perceived Stress Scale, can be utilized to judge improvement of symptoms as described herein. In another aspect, the symptom is cognitive sensory response, such as an electrofrequency hologram event-related potential, such as a mismatched negativity, an auditory P300 event-related potential, and/or a reduced gammaband auditory steady state response. These cognitive or sensory symptoms do not respond to available antipsychotic drugs. Although often effective at treating positive aspects of schizophrenia, schizoaffective disorder and similar disorders addressed above, antipsychotic drugs are largely ineffective at treating negative symptoms and in many aspects general symptoms, and attempts at use of antidepressants, such as selective serotonin reuptake inhibitors (SSRIs) and the like have not held promise. By "improved," "improving," or "improvement" in relation to a symptom of a disorder, disease, or condition, it is meant that a measurable metric or measurement of the symptom is moved towards a normal value for a patient and away from a value that is characteristic of the disease or condition. For example, improvement of the negative symptom of the patient being uncommunicative or minimally communicative and withdrawn would mean the patient is more communicative and engaging.

Provided herein are methods of treating various psychiatric disorders using a composition comprising a *W. somnifera* composition, e.g., an active agent, such as a composition prepared from the medicinal herb *W. somnifera*, often referred to as ashwagandha, and typically is in the form of an extract of *W. somnifera*. The *W. somnifera* agent, for example, the extract of, e.g., the roots and/or leaves of, a *W. somnifera* plant, are administered to improve symptoms of the psychiatric disorder as described above, and in one aspect to improve one or more negative symptoms of the psychiatric disorder, and optionally one or more general and/or one or more positive symptoms of the psychiatric disorder.

In one aspect, a method of treating a patient with a psychiatric disorder is provided. The psychiatric disorder includes psychotic disorders (or psychoses), and includes any disorder for which an antipsychotic drug is administered. Non-limiting examples of such disorders include: a schizophrenia disorder (295.xx according to DSM-IV-TRTM and DSM-5TM, and F20.9 according to International Classification of Disease, or ICD-10-CM codes); 295.30 Schizophrenia, Paranoid Type; 295.10 Schizophrenia, Disorganized Type; 295.90 Schizophrenia, Undifferentiated Type; 295.60 Schizophrenia, Residual Type; 295.70 (F25.0, F25.1) Schizoaffective Disorder; 295.40 (F20.81) Schizophreniform Disorder; 297.1 (F22) Delusional Disorder; 298.8 (F23) Brief Psychotic Disorder; 298.8 (F28) Other specified Schizophrenia Spectrum and other Psychotic Disorder; 298.9 (F29) Unspecified Schizophrenia Spectrum and other Psychotic Disorder. DM and ICD codes are provided for exemplary purposes only. In one aspect, the treated patient has an exacerbation of one or more symptoms, e.g., one or more negative, general, or cognitive/sensory symptoms of a psychiatric disorder of which an anti-psychotic drug is administered, such as schizophrenia or a schizophrenic disorder. The method comprises administering to the patient an amount of an antipsychotic drug and an amount of a composition comprising leaves and/or roots of a *W. somnifera* plant or an extract of, e.g., the roots and/or leaves of, a *W. somnifera* plant, or portions thereof, effective to treat the patient, e.g., to improve a negative symptom and/or a cognitive/sensory symptom of a psychiatric disorder of which an anti-psychotic drug is administered, such as schizophrenia or a schizophrenic disorder. In one aspect, the extract is prepared by alcohol-extraction of the roots and/or leaves of a *W. somnifera* plant. In another aspect, the extract is prepared by water-extraction of the roots and/or leaves of a *Withania somnifera* plant.

*Withania somnifera* Dunn. is also referred to as Ashwagandha in Ayurvedic medicine, or as to Indian *Ginseng*. It is reputed for promoting health and longevity by increasing defense against disease, arresting the aging process, revitalizing the body in debilitating conditions, and is often referred to as an adaptogen. Commercial preparations typically include ground roots and leaves, or extracts of roots and leaves. The roots and leaves of the *W. somnifera* plant, and extracts thereof, have the desired chemical constituents providing the extract its utility in the methods described herein. Nevertheless, although reference is made to the roots and leaves of the *W. somnifera* plant, other plant parts may find use in preparation of standardized extracts, so long as activity of the composition according to the methods described herein is retained, and toxicity is minimized.

Extracts of *W. somnifera* (WSE) have demonstrated immunomodulatory and anti-inflammatory actions in animal studies, enhancing type-1 immune response and cytokine production while modulating production of acute phase reactants, Cox 2 inhibition, and inhibition of NF-kB inflammatory signaling pathways. WSE has also shown anxiolytic, pro-cognitive, and anti-arthritic benefits and appears to have fairly good safety in early human studies. A WSE extract inhibited NF-kB (an inflammatory signaling pathway) in mononuclear cells from healthy controls and patients with rheumatoid arthritis, and also suppresses the production of several pro-inflammatory cytokines. WSE attenuates pro-oxidant and inflammatory activity in astrocytes and microglia. Based on animal and human immune-inflammatory data, it was posited that standardized extracts of *W. somnifera* would prove beneficial for recently exacerbated symptoms in patients with schizophrenia.

Figure 1A:
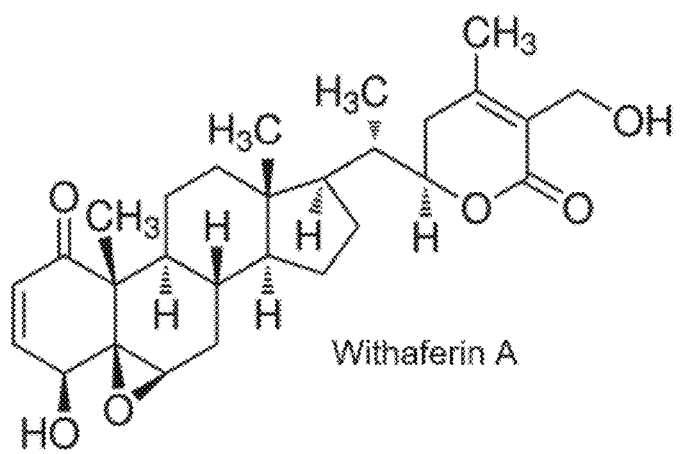
Figure 1B:
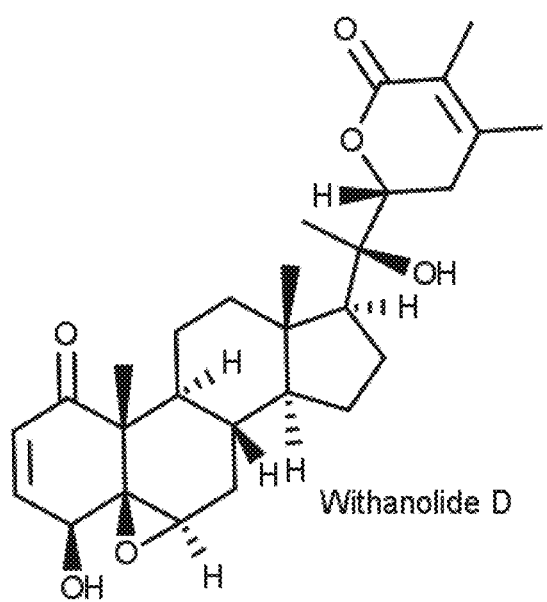
Figure 1C:
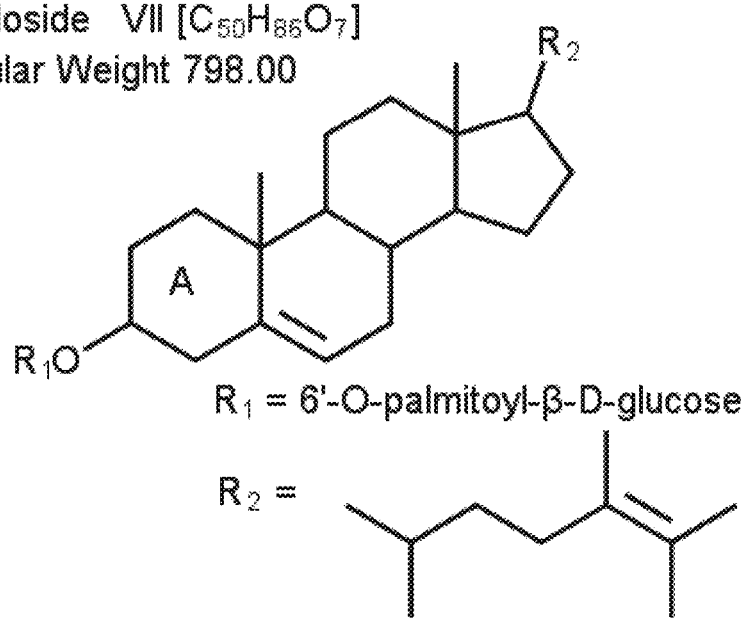
Figure 1D:
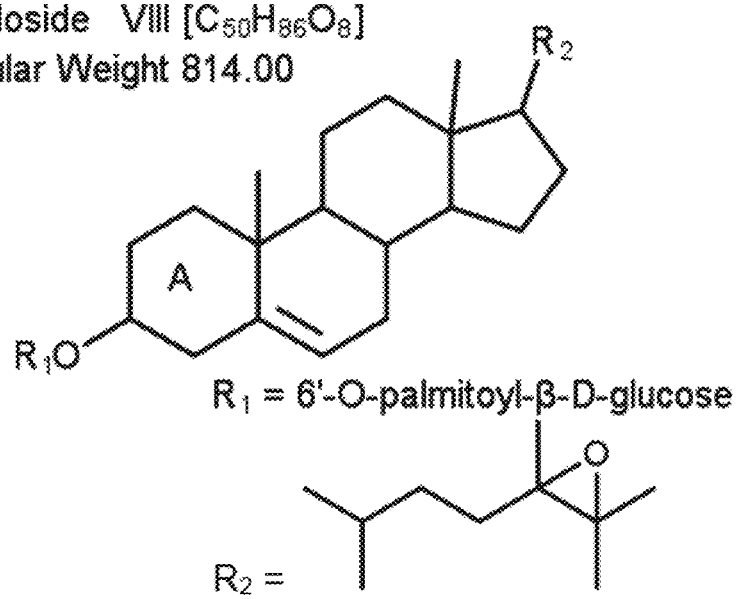
Figure 1E:
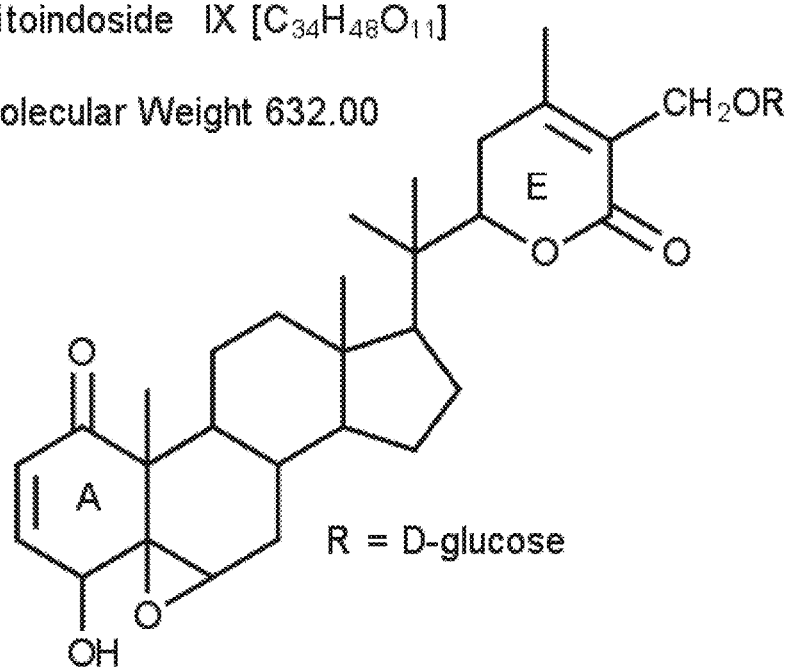
Figure 1F:
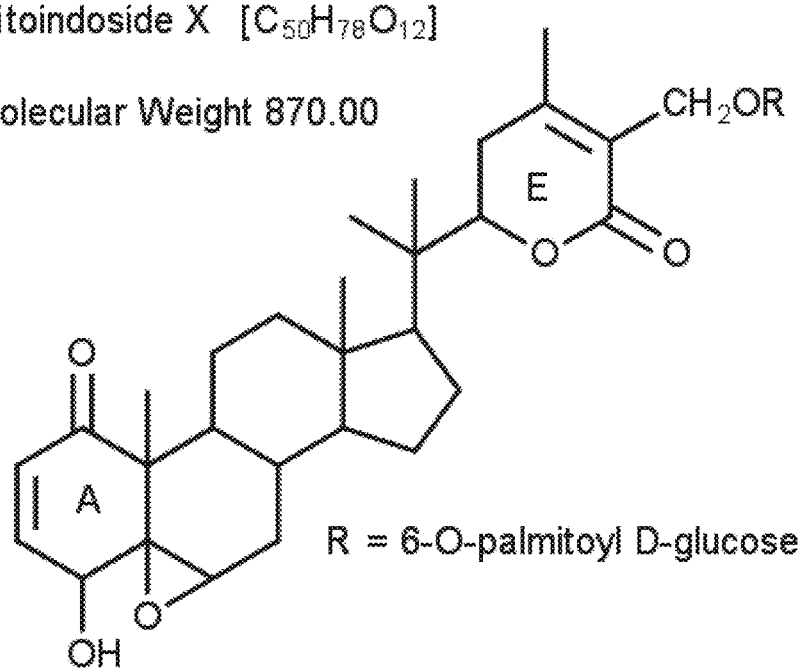

Various unique compounds are found within the extract of, e.g., the roots and/or leaves of, a *W. somnifera* plant, and can be obtained by either extraction or purification methods using parts of, e.g., the roots and/or leaves of, a *W. somnifera* plant, or by synthetic manufacture. Thus, leaves and/or roots of a *W. somnifera* plant or an extract of, e.g., the roots and/or leaves of, a *W. somnifera* plant comprise one or more "*W. somnifera* active agent", which comprises pharmacologically active compositions (active agents) found in the extract of, e.g., the roots and/or leaves of a *W. somnifera* plant, such as withanolide glycosides, sitoindosides, sapogenins, and oligosaccharides found therein, and aglycone derivatives thereof, such as withaferin A (aglycone), and derivatives thereof (see, e.g., U.S. Patent Application Publication Nos. 20040166184, 20130115316, and 20150320771, incorporated herein by reference). The *W. somnifera* active agents are useful in the methods of treating the psychological disorders described herein, such as schizophrenia, schizoaffective disorder, or other disorders for which antipsychotic drugs are prescribed. Chemical constituents, e.g., active agents, found in *W. somnifera*, and extracts thereof, such as aqueous or alcohol extracts, include the following: Withaferin A (FIG. 1A), Withanolide D (FIG. 1B), Sitoindoside VII (FIG. 1C), Sitoindoside VIII (FIG. 1D), Sitoindoside IX (FIG. 1E), and Sitoindoside X (FIG. 1F).

The following depicts a Withaferin A derivative (See, U.S. Patent Application Publication No. 20150320771):

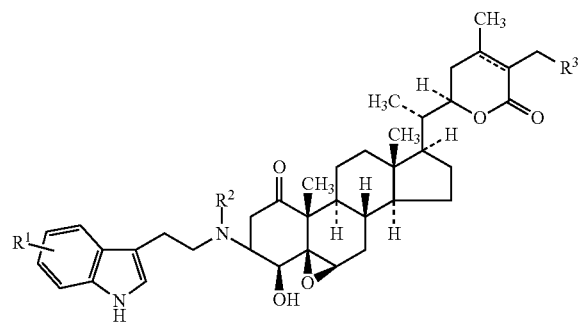

where $R^1$ is H, $C_1$-$C_3$ alkyl, or $C_1$-$C_4$ alkoxyl, $R^2$ is H or $C_1$-$C_3$ alkyl, $R^3$ is H or HO, and ≈≈≈≈≈ is a single or double bond. Methods of preparing the withaferin A derivative described above are described in U.S. Patent Application Publication Nos. 20130115316 and 20150320771.

Typically, commercially available extracts of *W. somnifera* lack the beneficial chemical constituents in appreciable quantities for which ashwagandha is reputed for, instead they contain: traces of glycowithanolide or are completely devoid of glycowithanolides; large amounts of withanolide aglycones; high levels of polysaccharides, and low levels of oligosaccharides; and toxic tropane-type alkaloids or scopolamine. The quality of *W. somnifera* extract is improved by using the process reported in the U.S. Pat. Nos. 6,153,198 and 6,713,092, and is a suitable process for obtaining the extract of *W. somnifera*. Additional uses for the extract of *W. somnifera*, and compositions containing the extract are described in U.S. Pat. Nos. 7,318,938, and 7,250,181. The extraction procedure provides an extract powder composition, which contains all the desired bioactive ingredients in optimized concentrations and ratios. The composition is stable, bio-available, and non-toxic.

In one aspect, an extract is prepared from *W. somnifera* plant parts. For example, on one aspect, dried roots and/or leaves from plants are water extracted, typically at a temperature of less than 60° C., at a suitable temperature, filtered and concentrated as needed, yielding a product comprising (e.g., by HPLC) at least 8% (as used herein w/w unless indicated otherwise) withanolide glycosides, at least 32% oligosaccharides, and at most 2% free withanolide aglycones (e.g., as withaferin A). When dried and powdered, a free-flowing brown to dark brown powder is formed that is approximately 97% soluble in water. In one aspect, capsules or tablets are prepared according to standard formulation methods known to those of ordinary skill in the pharmaceutical and formulary arts, including such excipients as microcrystalline cellulose, carboxymethylcellulose, and various preservatives, lubricants or flowing agents, anticaking agents, and dissolution enhancers, such as fumed silica. An exemplary product having these specifications is SENSORIL®, available from Natreon, Inc. of New Brunswick, N.J. In one example, a *W. somnifera* plant extract was prepared essentially as described above by aqueous extraction and stored under normal storage conditions and accelerated storage conditions, yielding withanolide glycoside ranges from 15.96% to 16.85%, Withaferin A ranges from 1.21% to 1.89%, and oligosaccharide ranges from 40.30% to 42.11%, indicating the stability of the composition.

Additional *W. somnifera* extracts, including indolealkylamino-withasteroid conjugates, useful for the methods and compositions described herein are described Using that procedure, any part of the plant of *W. somnifera* can be used to obtain the extract provided it is devoid or has a trace amount of toxic tropane-type alkaloid, scopolamine. Preferred extract is the standardized extract containing glycowithanolides, withanolide agylcone and oligosaccharides and devoid or have a only a trace amount of toxic tropane-type alkaloid.

The extraction procedure of U.S. Pat. No. 6,153,198 provides: a high purity *W. somnifera* plant extract composition with substantially low levels of cytotoxic withaferin A (aglycone), in the form of a stable, free-flowing light yellow-to-brown herbaceous powder composition. A typical dosage range for providing enhanced cognition and augmented learning facility in the geriatric population of the extract is from about 200 to 800 mg/day. The described biologically-enhancing composition described therein includes in one aspect, by weight, (a) at least 3% of withanolide glycosides and sitoindosides, (b) at least 3% of oligosaccharides, pe.g., with a mol. wt. of <2000, and (c) less than 0.5% of free withaferin A (aglycone), wherein the ratio of (a):(c) is 75-95:25-5 and the ratio of (a):(b) is 40-60:60-40. Preferably, the composition is at least 90% soluble, the ash content of this composition is less than 8%, and its moisture content is less than 5% (w/w).

The exemplary standardized extract reported in U.S. Pat. No. 6,713,092 is contained in Table 1.

TABLE 1 exemplary content of a standardized *W. somnifera* extract

| ANALYSIS | SPECIFICATION | RESULTS |
|---|---|---|
| Identity (HR) | HPLC - PDA spectrum | Confirms |
| i) Total withanolide glycoside conjugates (By HPLC) | ≥8% | 12.7% |
| ii) Oligosaccharides (By HPTLC) | ≥25% | 36.3% |
| iii) Free withaferin A and Equivalents - withanolide aglycones (By HPLC) | ≤2.0% | 1.60% |
| Heavy Metals (as PB) | ≤0.002% | Complies |
| Arsenic (As) | ≤0.0002% | Complies |
| Sulfated Ash | ≤8% | Complies |
| Moisture content | ≤5% | 3.50% |
| Microbiological Test | | |
| Total Aerobic plate count | <$10^3$/g | $2 \times 10^2$ CFU/gm |
| *Escherichia coli* | Absent in 1 g | Ni |
| *Salmonella* | Absent in 10 g | Nil |
| Ratio of withanolide glycoside conjugates and free withaferin A (aglycones) | 75-95 to 25-5 | 89:11 |
| Ratio of withanolide glycoside conjugates and oligosaccharides | 12-35 to 82-65 | 26:74 |
| PRODUCT DESCRIPTION | Appearance | Fine Powder |
| | Color | Brown to brownish green |
| | Odor | Characteristic |
| | Taste | Mild bitter |
| | Water-soluble extractive value | ≥80% |

In aspects, the *W. somnifera* extract composition comprises 8% or greater withanolide glycosides and sitoindosides, 32% or more of oligosaccharides, e.g., from 45%, to 60%, or from 45% to 55% of oligosaccharides and 2% or less of withaferin A, e.g., from 0.15% to 0.30%, e.g., from 0.19% to 0.30% withaferin A (all by HPLC).

Antipsychotic drugs, as used herein are a class of drugs often used to treat positive symptoms of schizophrenia, schizoaffective disorder and similar disorders addressed above. Table 2 provides examples of commonly-prescribed antipsychotic agents, and typical, exemplary, and non-limiting prescribed oral dosage ranges. Table 3 provides examples of commonly-prescribed antipsychotic agents, and typical, exemplary, and non-limiting prescribed intramuscular (IM) dosage ranges.

TABLE 2 oral antipsychotic medications

| Generic name | Examples of Brand names | Commonly-Prescribed Oral Dose ranges |
|---|---|---|
| Atypical Antipsychotics | | |
| asenapine | SAPHRIS ® | 5 mg-20 mg daily |
| quetiapine | SEROQUEL ® | 150 mg-800 mg daily |
| lurasidone | LATUDA ® | 20 mg-160 mg daily |
| olanzapine | ZYPREXA ® | 5 mg-25 mg daily |

TABLE 2-continued oral antipsychotic medications

| Generic name | Examples of Brand names | Commonly-Prescribed Oral Dose ranges |
| --- | --- | --- |
| iloperidone | FANAPT ® | 12 mg-24 mg daily |
| paliperidone | INVEGA ® | 3 mg-12 mg daily |
| aripiprazole | ABILIFY ® | 2 mg-30 mg daily |
| brexpiprazole | REXULTI ® | 2 mg-4 mg daily |
| risperidone | RISPERDAL ® | 1 mg-8 mg daily |
| cariprazine | VRAYLAR ® | 1.5 g-6 mg daily |
| ziprasidone | GEODON ® | 40 mg-160 mg daily |
| Clozapine | CLOZARIL ® | 100 mg-900 mg daily |
| Miscellaneous antipsychotics | | |
| Pimozide | ORAP ® | 1 mg-10 mg daily |
| Molindone | MOBAN ® | 20 mg-225 mg daily |
| Loxitane | LOXAPINE | 60 mg-250 mg daily |
| Haloperidol | HALDOL ® | 1 mg-30 mg daily |
| Phenothiazine antipsychotics | | |
| Chlorpromazine | THORAZINE ® | 200 mg-800 mg daily |
| Trifluoperazine | STELAZINE | 15 mg-40 mg daily |
| Perphenazine | TRILAFON | 12 mg-32 mg daily |
| Fluphenazine | PROLIXIN ® | 5 mg-40 mg |
| thioridazine | MELLARIL ® | 200 mg-800 mg daily |
| Thioxanthenes | | |
| Thiothixene | NAVANE ® | 20 mg-60 mg daily |

TABLE 3 injected (IM), long-acting antipsychotic medications

| Generic name | Commonly-Prescribed Dosages |
| --- | --- |
| Fluphenazine Decanoate | 6.25 to 50 mg IM Q 2 weeks |
| Haloperidol Decanoate | 75 to 200 mg IM Q 4 weeks |
| Risperidone (RISPERDAL CONSTA ®) | 12.5 to 50 mg IM Q 2 weeks |
| Paliperidone palmitate (INVEGA SUSTENNA ®) | 39 to 234 mg IM Q 4 weeks |
| Paliperidone palmitate (INVEGA ® TRINZA) | 273 to 819 mg IM Q 12 weeks |
| Aripiprazole (ABILIFY MAINTENA ®) | 300 to 400 mg IM Q 4 weeks |
| Aripiprazole (ARISTADA ®) | 441 to 882 mg IM Q 4 weeks (or 882 mg IM Q 6 weeks, or 1064 mg IM Q 2 months) |
| Olanzapine (ZYPREXA ® RELPREV) | 150 to 405 mg IM Q 2 or 4 weeks |

*IM = intramuscular

As above, the amount of *W. somnifera* active agent, e.g., extract, administered to a patient is an amount effective to achieve relief or improvement of one or more symptoms of schizophrenia, schizoaffective disorder, or any other condition for which an antipsychotic drug is administered to a patient. The *W. somnifera* plant material or extract thereof can be administered concurrently with the antipsychotic drug, though not necessarily.

In one aspect, a dosage form composition is provided including an antipsychotic drug and a *W. somnifera* active agent, e.g., an extract of *W. somnifera* plant material, such as an extract of roots and/or leaves, in amounts effective to treat schizophrenia, schizoaffective disorder, or a condition for which an antipsychotic drug is prescribed.

The active agents, e.g., in the form of compounds or extracts, may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one aspect, the dosage form is an oral capsule, liquid, or table prepared according to standard methods and with standard excipients, as are broadly-known in the pharmaceutical arts. The capsule, tablet, liquid, or other oral dosage form may be designed to release the active ingredients contained therewithin as a bolus or over time, and the active ingredients can be distributed within the dosage form, and within the materials used to make up the dosage form for extended delivery, or for delivery at different time frames post-ingestion. Extended-release oral dosage forms are prepared according to well-known techniques in the pharmaceutical arts. In another, the composition is an intramuscular or intravenous dosage form, and includes a sterile solution comprising the active ingredients, and a solvent, such as water, saline, lactated Ringer's solution, or phosphate-buffered saline (PBS). Additional excipients, such as polyethylene glycol, emulsifiers, salts, rheology modifiers, and buffers may be included in the solution. In another aspect, the dosage form is a spray or aerosol for inhaled or nasal administration, as are known in the pharmaceutical arts.

Example 1

A randomized, double-blind, placebo controlled study was performed based on a total of 66 patients with Schizophrenia or Schizoaffective Disorder who were experiencing an exacerbation of symptoms, and the efficacy data is based on n=33 subjects who received the Standardized extract of *W. somnifera*—SENSORIL® n=33, and n=33 who received placebo, the treatment was provided for 12 weeks. The dosage of SENSORIL®—Standardized Extract of *W. somnifera* was titrated from 500 mg/day for the first week to 1000 mg/day for the balance of the study.

The dosage of the Standardized Extract of *W. somnifera*—SENSORIL® was adjusted as follows: 250 mg by mouth twice daily (i.e., total daily dosage of 500 mg/day) for one week, and then increased to 500 mg by mouth twice daily (i.e., total daily dosage of 1000 mg/day) for the balance of the study, i.e., 11 weeks. The capsules were taken with water or juice and patients were advised to take it with food and not on an empty stomach.

Positive, negative, and general symptoms are added up to come up with a total symptom score. One of the common scales to measure change in clinical trials in schizophrenia and/or schizoaffective disorder is the Positive and Negative Syndrome Scale—PANSS, and this scale was used to measure symptoms and improvements in the study on which the treatment claims are based. Subscales within the PANSS scale capture the Positive, Negative, General and Total symptoms. The symptoms of perceived stress were measured using the Perceived Stress scale which is also widely used in several studies.

When added to antipsychotic drugs (taken for at least 4 weeks or more) in men or women aged 18 years or older with a diagnosis of Schizophrenia or Schizoaffective Disorder who have experienced an exacerbation of symptoms, a Standardized Extract of *W. somnifera*—SENSORIL® provided significant benefits for Negative, General and Total symptoms compared to those receiving a placebo.

In these same patients, the same Standardized Extract of *W. somnifera*—SENSORIL® also significantly improves scores on a known stress scale compared to those receiving a placebo.

The time to onset of improvements in Negative, General and Total symptoms for the above patients were first noticed at 4 weeks after—SENSORIL® was started, and continued throughout the 12 weeks of treatment with—SENSORIL®.

The time to onset of improvement in stress scores in the same patients with—SENSORIL® also followed the same time course as the Negative, General and Total symptoms.

During the 12 week study, in the group that received the Standardized Extract of *W. somnifera*—SENSORIL®, there were significantly fewer dosage adjustments of anti-psychotic drug doses (or the addition of a second antipsychotic drug) compared to those who received placebo.

In further detail, sixty-six randomized patients (n=33 per group) provided efficacy data. Beginning at 4 weeks, and continuing to the end of treatment, WSE produced significantly greater reductions in PANSS negative, general and total symptoms (Cohen's d: 0.83, 0.76, 0.83), but not positive symptoms, when compared to placebo. PSS scores improved significantly with WSE treatment compared to placebo (Cohen's d: 0.58). CRP and S100B declined more in the WSE group but were not significantly different from placebo. Adverse events were mild to moderate and transient; somnolence, epigastric discomfort, and loose stools were more common with WSE. In conclusion, this study suggests that adjunctive treatment with a standardized extract of *Withania somnifera* provides significant benefits for negative, general, total, and stress symptoms in recently exacerbated patients with schizophrenia.

Methods

Patients included male or female outpatients aged 18 to 75 years of any race, with DSM IV-TR Schizophrenia or Schizoaffective Disorder affirmed by the Mini International Neuropsychiatric Interview (MINI, Sheehan, D. V., et al. The Mini-International Neuropsychiatric Interview (M.I.N.I.): the development and validation of a structured diagnostic psychiatric interview for DSM-IV and ICD-10, *J Clin Psychiatry.* 1998; 59 Suppl 20:22-33) and supplemented by history from medical records and referring clinicians, were recruited. All subjects provided written informed consent. At study entry, the Positive and Negative Syndrome Scale (PANSS) total score had to be ≥60, with a score of ≥5 on any one of the items of the positive symptom cluster (delusions, conceptual disorganization, hallucinatory behavior, excitement, grandiosity, suspiciousness/persecution, hostility), or unusual thought content. Alternatively, a score of at least 4 on any two items of this symptom cluster qualified patients for study inclusion. Moreover, symptom exacerbation had to extend greater than two weeks, but less than one year and patients had to be receiving antipsychotic agents for at least 4 weeks. Women in the reproductive age group were required to have a negative pregnancy test at entry. Additional exclusion criteria included positive tests for illicit drugs (marijuana and alcohol use were allowed on a case by case basis), unstable medical disorders, pregnancy or breastfeeding, known allergy to WSE, or conditions requiring immediate psychiatric or medical hospitalization. Subjects receiving antibiotics, antiviral or anti-parasitic medications; those receiving immunosuppressive therapy; and subjects taking daily NSAIDs or doses of aspirin greater than 81 mg/day were excluded.

The study was a 12-week, double-blind, randomized, placebo-controlled trial of a standardized extract of WSE (SENSORIL®, target dosage: 1000 mg/day) added to ongoing antipsychotic treatment in moderately symptomatic patients with either schizophrenia or schizoaffective disorder.

Subjects meeting all eligibility criteria progressed to a 1:1 randomization to WSE or placebo. A computerized randomization schedule was generated, and IDS (Investigational Drug Service) secured the study medications and blinded codes. All assessments were conducted double-blind (rater and patient blinded). The WSE and placebo were constituted as identical gelatin capsules. The WSE capsules contained 250 mg of the standardized extract along with inactive ingredients, including cellulose, croscarmellose, silicon dioxide, magnesium citrate, and others. The placebo capsules had the same inactive ingredients and fill weight as the WSE capsule but did not contain the WSE extract. To mask the smell of the WSE capsules, the placebo capsules were exposed to fully closed cloth pouches that contained WSE powder. After a couple of days, the odor permeated the placebo capsules, making them smell like the WSE capsules. Study medication or placebo was initiated on day 1 by oral route and was given BID. At this stage, the active group received 250 mg of WSE twice a day for a total daily dose of 500 mg/day. This was titrated to 500 mg BID, for a total daily dose of 1000 mg/day, at week 2. This dosage was maintained for the rest of the study, unless tolerability dictated a lower dosage. Pill counts and reconciliation at each visit served as a measure of adherence. Including the screening visit, there were a total of 6 visits. The treatment period with study medication was 12 weeks.

The primary outcomes were assessed using the Positive and Negative Syndrome Scale (Kay S. R. et al., Fiszbein A, Opler LA: The positive and negative syndrome scale (PANSS) for schizophrenia. Schizophr Bull. 1987; 13:261-276). Secondary outcomes included the Perceived Stress Scale (PSS, Cohen et al, 2000), which evaluated stress levels of subjects during the study, and the Clinical Global Impressions Scale, to determine any improvement. These assessments were conducted at every visit during the study. Immune-inflammatory laboratory measures included the cytokines IL-2, IL-4, IFN-γ, and IL-6, as well as hsCRP and S100B; these were measured in serum at screening and at the end of treatment. The cytokines were assayed using a multiplex Luminex® bead technology assay (Invitrogen, Camarillo, Calif.). The lower limit of detection sensitivity of the assay for human IL-2 was <6 pg/mL, IL-4 was <5 pg/mL, IL-6 was <3 pg/mL, and IFN-γ was <5 pg/mL. High sensitivity C-reactive protein (hs-CRP) was measured in mg/L units using a nephelometric method that employed latex particles coated with CRP monoclonal antibodies. The lower limit of detection sensitivity of this commercially available assay (Quest Diagnostic Labs) is 0.2 mg/L. S100B was measured in serum in picograms/ml using a commercially available sandwich ELISA (EMD Millipore, Mass., USA). The lower limit of detection sensitivity of the 5100B assay was 2.7 picograms/ml with the intra- and inter-assay CVs being <4.8% and 4.4% respectively.

The primary efficacy measure was change from baseline to end of the treatment in PANSS total and PANSS positive, negative and general symptoms scores. Secondary efficacy measures included proportions of patients in each treatment group meeting at least 20% improvement in PANSS total, positive, negative, and general symptom scores. Baseline to end of treatment PSS total scores and proportions in each treatment group achieving at least 20% improvement in PSS scores were also secondary efficacy outcomes. Furthermore, time to onset of any improvements in PANSS or PSS scores (i.e. change from baseline to each visit) between treatments was assessed as a secondary outcome as were proportions of patients showing improvement on the CGI-improvement subscale at the end of treatment.

Additional secondary outcomes assessed psychotropic medication changes, i.e. increase in antipsychotic drug dosage, switch of antipsychotic drug, or the addition of a second antipsychotic medication between treatments. Similar changes in mood stabilizers, anxiolytic/hypnotics, or anti-depressants were also evaluated. Changes in levels of hsCRP, S100B, and cytokines from baseline to end of treatment determined if WSE significantly diminished inflammatory-immune indices compared to placebo, and whether any reductions mediated improvement in clinical outcomes.

In the absence of prior data for WSE in treating symptoms of schizophrenia, we adopted a recommendation that a sample size of 40 to 100 subjects in adjunctive treatment trials in schizophrenia could provide reasonable guidance for initial studies. Moreover, initial positive studies with celecoxib or aspirin had sample sizes ranging from 50 to 70 subjects. An intent-to-treat analysis was planned of all subjects who were randomly assigned to either WSE or placebo, and who had at least one pre- and post-randomization primary efficacy outcome measure (PANSS total and subscale scores). For the primary efficacy analyses, a student's t-test was used to examine differences between treatment groups in changes from baseline to end of treatment in PANSS (total and subscale scores) and PSS scores in the intent-to-treat sample. A mixed-model repeated measures analysis using an auto-regressive covariance matrix examined the robustness of the primary analyses and the time to improvement in PANSS and PSS scores from baseline to end of treatment. This model used treatment, visit and treatment*visit interaction as fixed effects and subjects as random effects.

Secondary outcomes included proportions of subjects in each treatment group who achieved ≥20% improvements and were compared using a chi-square test. Cohen's d (effect size) was determined using the group mean change between treatment and placebo from baseline to study endpoint, divided by the pooled standard deviation. The number needed to treat (NNT) for ≥20% response rates was calculated as 100/absolute risk reduction. Proportions of subjects in each treatment group who experienced anti-psychotic or other psychotropic medication changes were compared using Fisher's exact test. Two-tailed hypotheses testing was conducted, and a p value of ≤0.05 was considered statistically significant. Statistical analyses was undertaken blind to treatment assignment.

As distributions of cytokine, hs-CRP or S100B levels are often skewed or affected by the lower limits of the detection sensitivity of the assays, it was planned to transform the data to normalize the distribution and/or use non-parametric statistics such as the Mann-Whitney U or Wilcoxon Signed Rank Tests to test statistical significance between or within treatment groups respectively. Immune/inflammatory changes were compared with changes in PANSS (subscales and total) and PSS scores using Pearson's or Spearman's correlations. Safety analyses of vital signs, EKG, laboratory measures, and body weight were evaluated either as continuous or categorical variables (for instance—normal, abnormal etc.). Reported treatment-emergent adverse events were grouped by organ-system and tabulated by treatment assignment, and rates between treatments were compared using chi-square or Fishers Exact test for categorical variables and t-tests for continuous variables.

Results 82 subjects were screened for consent and eligibility, and 68 subjects were randomly assigned to WSE (n=34) or placebo (n=34). One subject in each treatment group did not take the allocated treatment and provided no further data. Therefore, sixty-six patients (n=33 subjects in each treatment arm) formed the efficacy defined intent to treat population. Fifty-nine subjects (89.4%) completed the study, 28 (84.9%) in the WSE group and 31 (93.9%) in the placebo arm, with no statistically significant differences between treatments.

None of the demographic, illness or medication characteristics (Table 4) differed significantly between the treatment groups. Patients comprised a cohort in their mid to late 40 s, mainly with a DSM-IV-TR diagnosis of Schizophrenia (61%), and with at least 20 years of illness and more than seven life-time hospitalizations. The mean duration of the current symptom exacerbation was nearly 16 weeks. On average, patients were obese (Body Mass Index just over 30 mg/kg2), and 62% were current cigarette smokers. The majority of patients in either treatment group (87.9% in WSE, and 90.9% Placebo) received atypical antipsychotic agents in similar daily olanzapine equivalents (Leucht S. et al., Dose Equivalents for Antipsychotic Drugs: The DDD Method. *Schizophr Bull* 2016; 42:S90-S94), and four subjects each in the WSE and in the placebo group received more than one antipsychotic agent. Five WSE and three placebo assigned subjects received clozapine. Other psychotropic agents, including anti-depressants, mood-stabilizers, anxiolytics, hypnotic-sedatives and anti-cholinergic agents were fairly evenly distributed between treatment groups. Adherence ranged from 82% to 100% among the majority of patients (63/66), with no significant differences between the two treatment groups.

TABLE 4

Demographic, Illness and Medication Characteristics

| | SENSORIL ® (n = 34) | Placebo (n = 34) | t-test or $X^2$, df, p |
|---|---|---|---|
| Age, mean (SD), y | 45.18 (12.90) | 47.38 (11.37) | 0.75, 66, ns* |
| Gender, male/female, n | 21/13 | 14/20 | ns |
| Race, White/African American, n | 12/22 | 20/14 | ns |
| Diagnosis, Schizophrenia/ Schizoaffective, n | 21/13 | 18/16 | ns |
| Age at onset of $1^{st}$ episode, mean (SD), y | 24.32 (10.89) | 24.00 (7.67) | 0.14, 66, ns |
| Number of lifetime psychiatric hospitalizations, mean (SD) | 7.71 (6.45) | 7.76 (6.90) | 0.04, 66, ns |
| Duration of illness, mean (SD), y | 20.85 (12.26) | 23.38 (11.61) | 0.83, 66, ns |
| Duration of current symptoms, mean (SD), weeks ** | 16.91 (11.02) | 14.84 (11.12) | 0.75, 62, ns |
| Smokers (current smokers) n (%) ** | 22 (67) | 19 (58) | ns |
| Body Mass Index, BMI, mean (SD) $kg/m^2$ | 30 (7.56) | 30.33 (8.04) | 0.17, 64, ns |

TABLE 4-continued

Demographic, Illness and Medication Characteristics

| | SENSORIL ® (n = 34) | Placebo (n = 34) | t-test or $X^2$, df, p |
|---|---|---|---|
| Psychotropic Medications ** | | | |
| Atypical Antipsychotics, n | 28 | 31 | ns 0.33, 57, ns |
| OLZ* Equivalent (SD), mg/day | 16.39 (8.21) | 17.37 (13.64) | |
| Typical Antipsychotics, n | 7 | 8 | ns |
| Antidepressants, n | 14 | 17 | ns |
| Mood Stabilizers, n | 9 | 13 | ns |
| Anti-anxiety, n | 10 | 11 | ns |
| Hypnotic/Sedative, n | 7 | 5 | ns |
| Anti-Cholinergic, n | 8 | 11 | ns |

*ns = statistically not significant,
** n = 33 in each group, $X^2$ or Fisher's Exact Test, OLZ = Olanzapine As noted in FIG. 2 the WSE treated group achieved significantly better outcomes on the PANSS negative, general and total symptom scores compared to those assigned to placebo. Treatment effect sizes favoring WSE ranged from large (negative and total symptoms, Cohen's d=0.83) to medium (general symptoms, Cohen's d=0.76, Cohen J. Quantitative Methods in Psychology, A Power Primer. Psychological Bulletin, 1992, Vol. 112. No. 1, 155-159) (Table 5). PANSS positive symptom scores improved more in the WSE group compared to placebo but did not achieve statistical significance (Cohen's d=0.48).

TABLE 5

Effect sizes and number needed to treat (NNT) for PANSS and PSS in favor of Sensoril

| | Cohen's d | Size of Effect |
|---|---|---|
| PANSS Positive | 0.48 | Small |
| PANSS Negative | 0.83 | Large |
| PANSS General | 0.76 | Medium |
| PANSS Total | 0.83 | Large |
| PSS Total | 0.58 | Medium |
| | NNT | 95% CI |
| PANSS Positive ≥20% | 6 | ARR extends from –ve to +ve |
| PANSS Negative ≥20% | 3 | 1.7 to 6.7 |
| PANSS General ≥20% | 4 | 1.9 to 13.2 |
| PANSS Total ≥20% | 4 | 1.9 to 13.5 |
| PSS ≥20% | 4 | 1.9 to 12.7 |

PANSS = Positive and Negative Syndrome Scale, PSS = Perceived Stress Scale, Effect Sizes: small >0.2 to 0.5, medium >0.5 to 0.8, Large >0.8 or greater, CI = confidence intervals, ARR = absolute risk reduction.

Figure 3A:
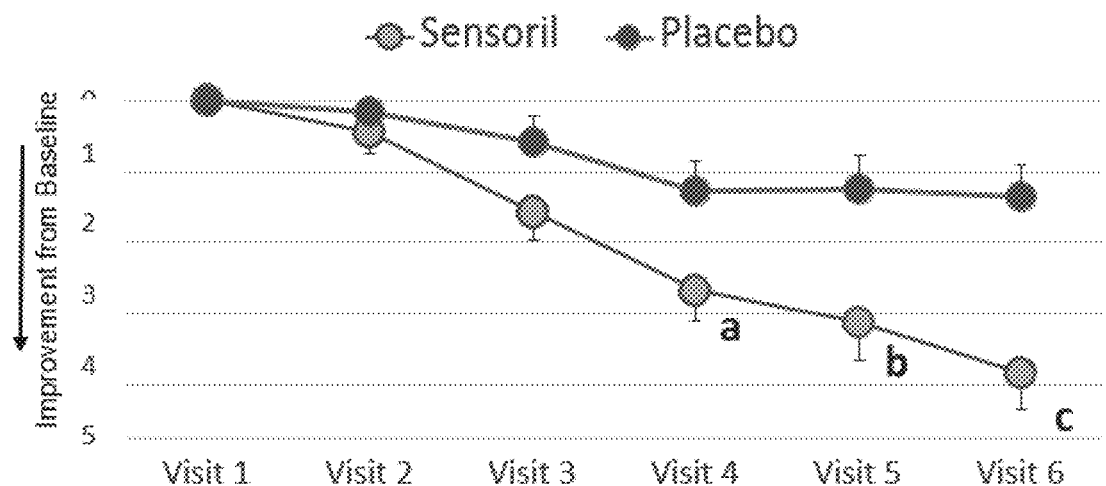
Figure 3B:
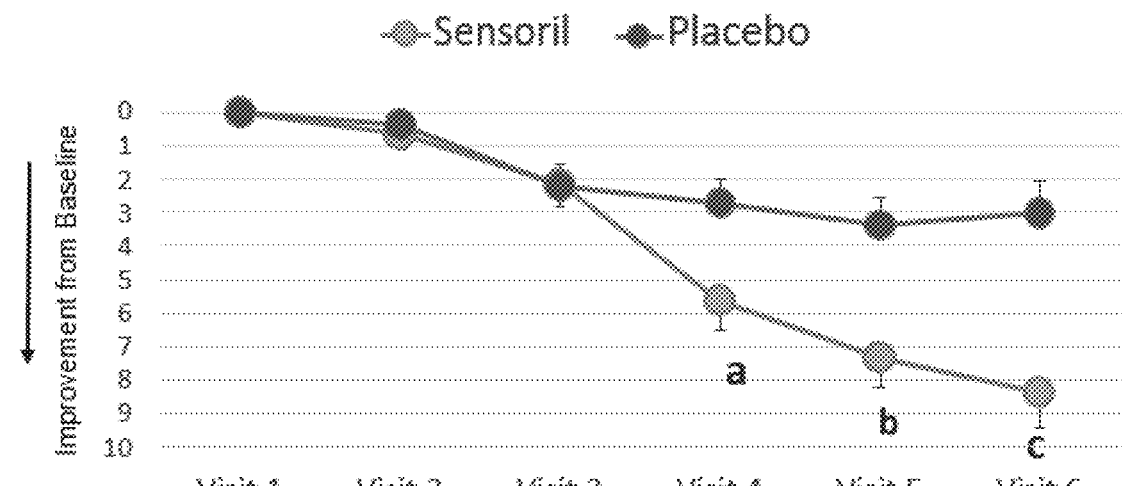
Figure 3C:
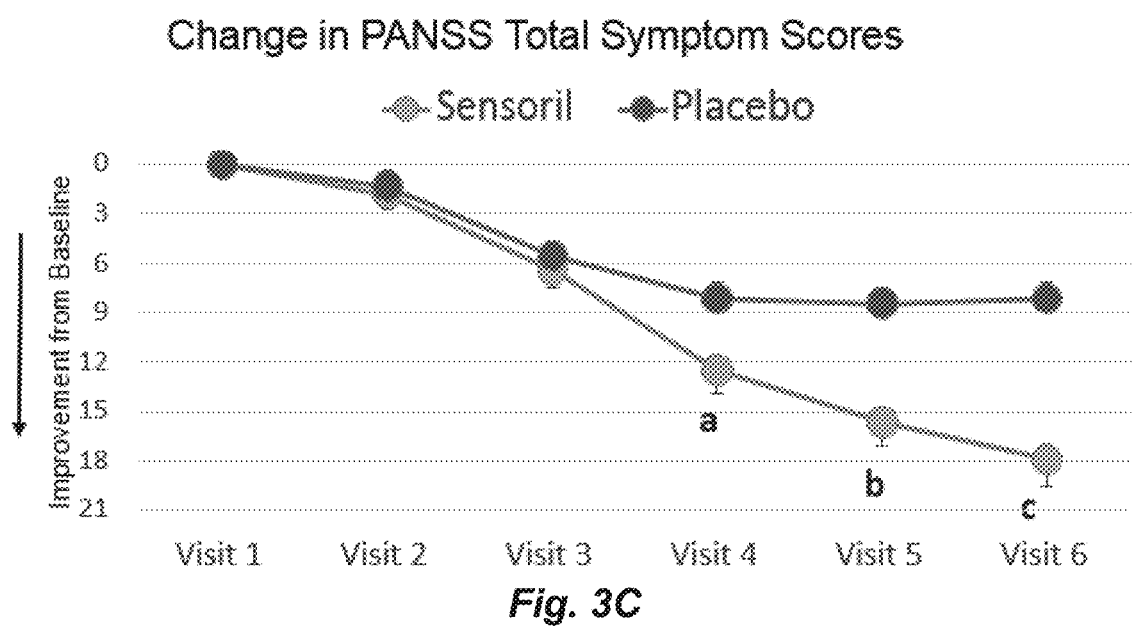
Figure 3D:
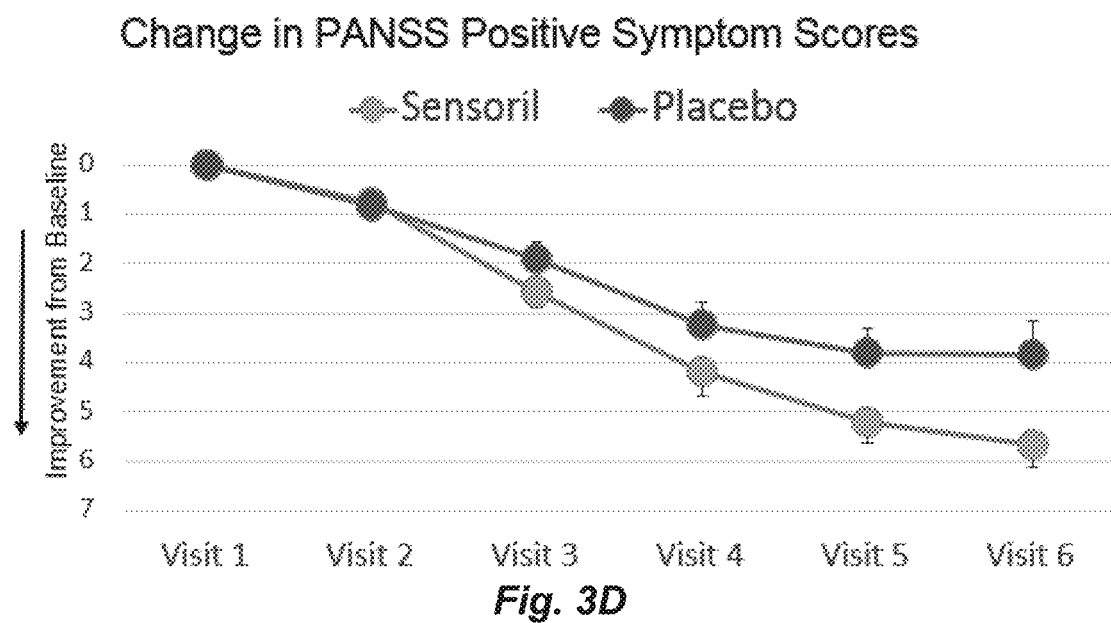
Figure 4:
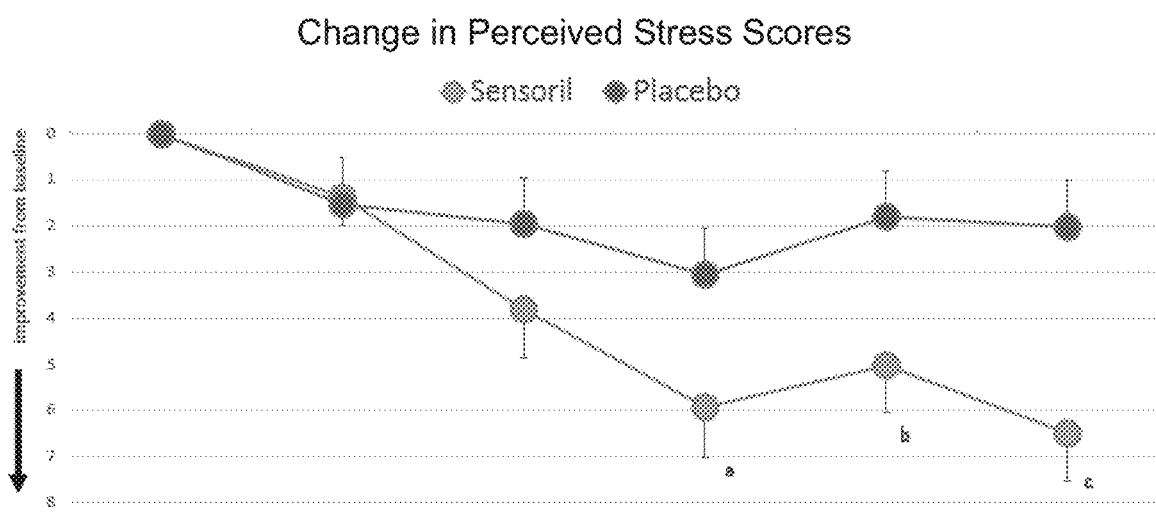
FIG. 4 is a graph showing changes in Perceived Stress Scores in Patients receiving *W. somnifera* Extract or Placebo, Visit 4, p=0.025, Visit 5 p=0.051, Visit 6 p=0.004.

Secondary Outcomes WSE treated subjects experienced significant reductions in PSS stress scores compared to placebo (Cohen's d=0.58) (FIG. 2 and Table 5). The time to significant separation in PANSS negative, general and total symptom scores favoring WSE over placebo began at Visit 4 (i.e. at four weeks of treatment) and was sustained throughout the remainder of the twelve week study (FIGS. 3A, 3B, 3C). A similar time course of improvement was noted in the PSS scores for the WSE group (FIG. 4).

Figure 5A:
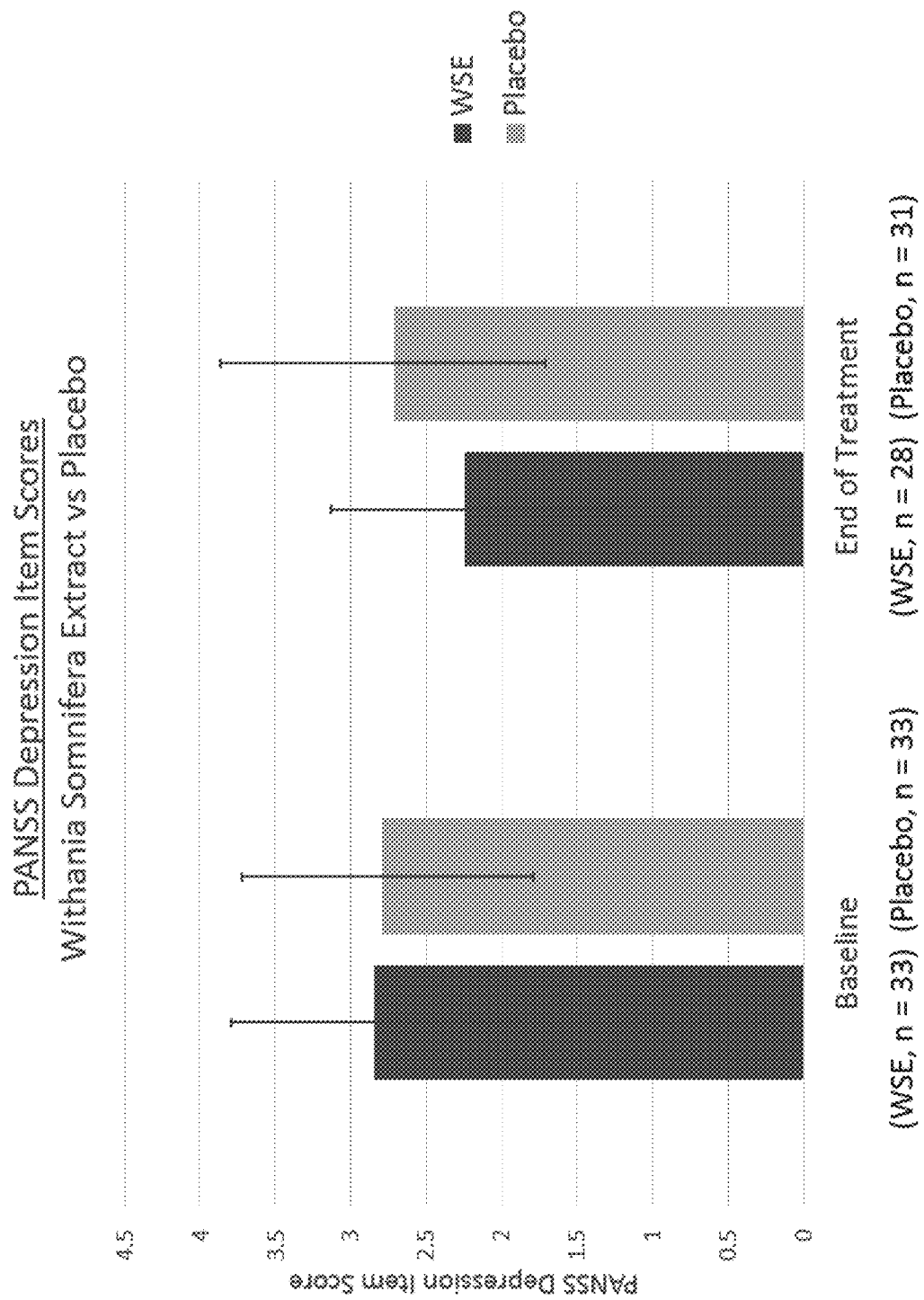
FIGS. 5A-5C are graphs showing depression, anxiety, and excitation scores, respectively, in patients receiving *W. somnifera* Extract or placebo for patients in Example 1.
Figure 5B:
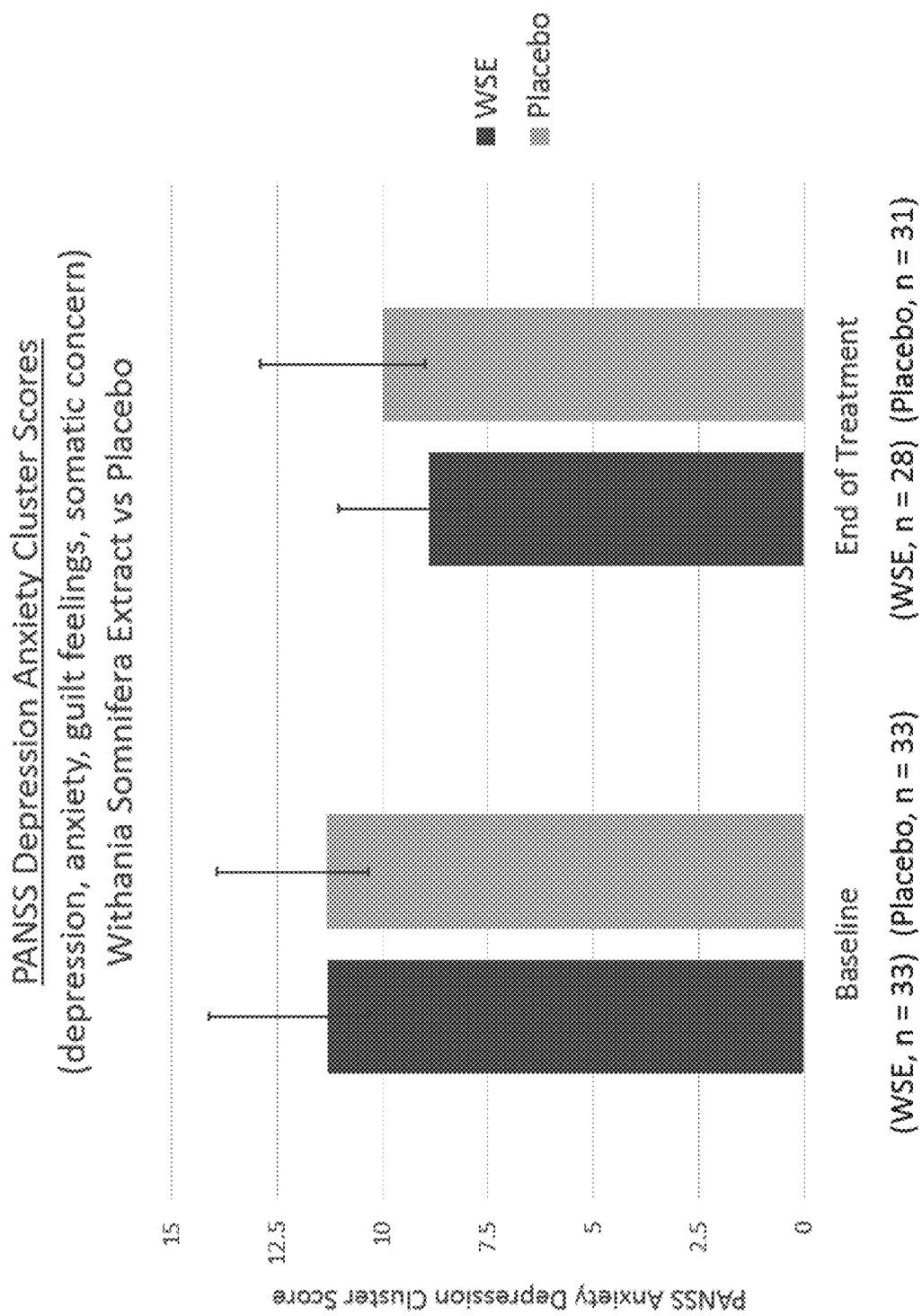
Figure 5C:
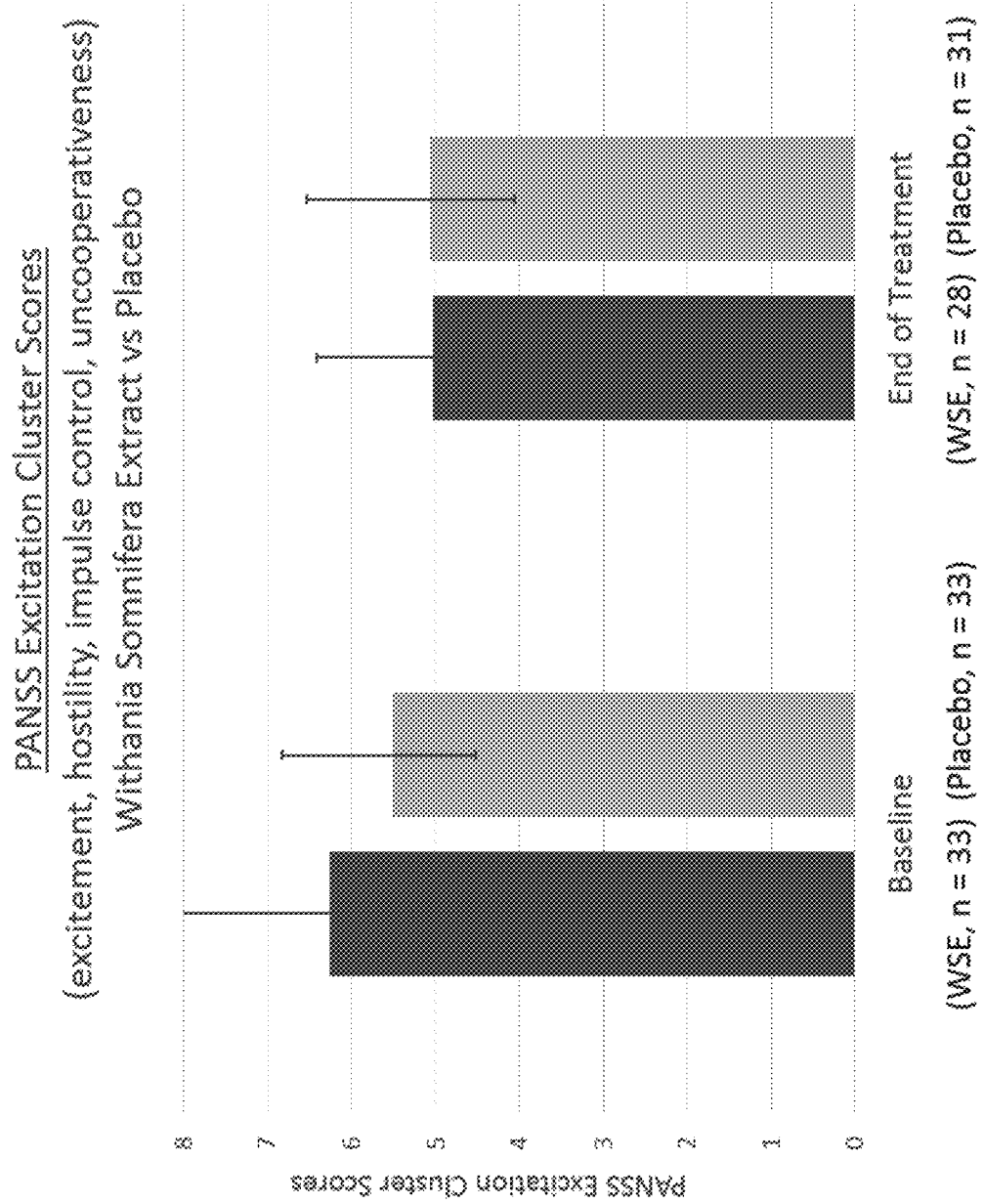

Further analyses of the general symptoms of the PANSS scale was conducted to assess if the depression score (single item on the PANSS scale) or the depression-anxiety cluster score (depression, guilt feelings, anxiety and somatic concern items on the PANSS scale) or the excitation cluster scores (excitement, poor impulse control, uncooperativeness and hostility items on the PANSS scale) improved in favor of Sensoril versus placebo. Such sub-analyses of the PANSS general symptoms scores has been evaluated for anti-psychotic drugs (e.g. Pueskens J, Van Baalen B, De Smedt C et al. International Clinical Psychopharmacology, 2000, 15:343-349). In all three analyses, improvements from baseline to end of treatment significantly favored Sensoril over placebo, with medium effect sizes (Cohen's d=0.68 for depression, 0.65 for the depression/anxiety cluster and 0.65 for the excitation cluster), see FIGS. 5A-5C.

WSE treated patients were significantly more likely to achieve 20% improvements in PANSS negative, general and total symptom scores, but not positive symptom scores, compared to those assigned to placebo (Table 5). The number needed to treat (NNT) to achieve one additional such outcome with WSE ranged from three for negative symptoms (95% CI: 1.7 to 6.7), to four for general (95% CI: 1.9 to 13.2) and total symptoms (95% CI: 1.9 to 13.5) (Table 5). Twenty percent or greater improvement in PSS stress scores also favored the WSE group compared to placebo (Table 5), and the NNT to achieve one additional such outcome was four (95% CI: 1.9 to 12.7) (Table 5). The proportion of patients rated as improved on the CGI-Improvement subscale by the end of treatment did not differ significantly between treatments (WSE: 12/33 (36.4%) vs. Placebo: 8/33 (24.2%)).

Use of Antipsychotic and Other Psychotropic Medications Nine (27.3%) of the placebo assigned subjects either had their antipsychotic drug dosage increased (n=8) or had a second antipsychotic drug added (n=1). By comparison, two (6.1%) WSE treated subjects had their antipsychotic drug dosage increased (Fisher's exact p=0.044). Other psychotropic medication changes were few and were not significantly different between treatments.

Figure 6:
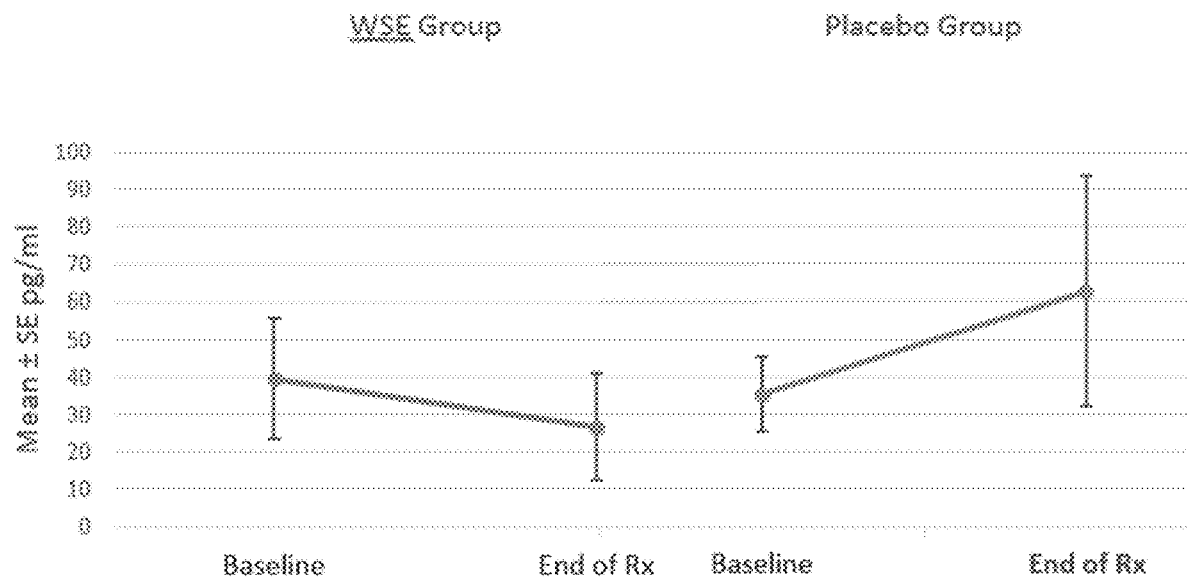
FIG. 6 is a graph showing changes in S100b Levels in Patients receiving *W. somnifera* Extract or Placebo for patients in Example 1.
Figure 8B:
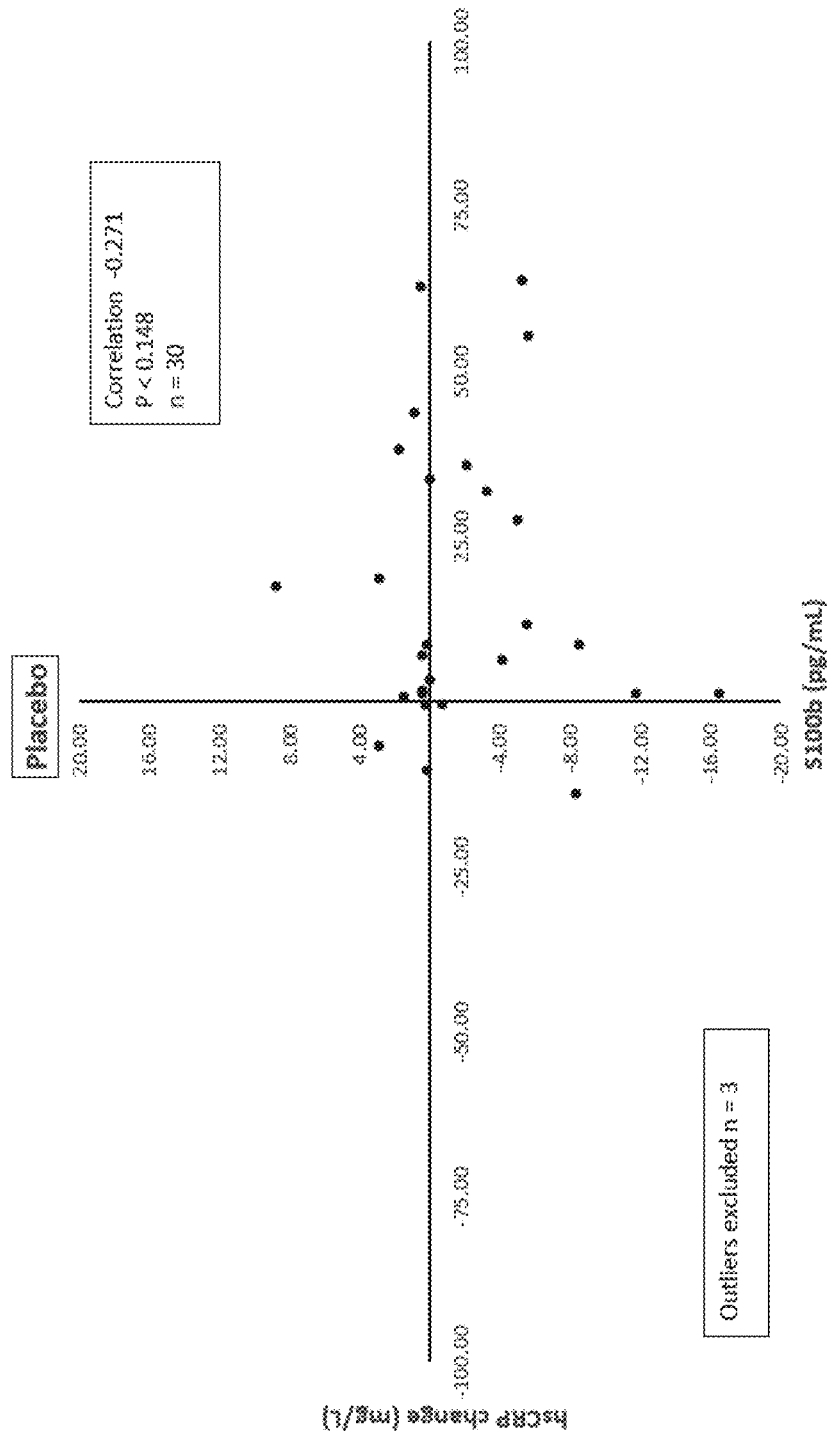

Inflammation Markers hsCRP and S100B levels declined in the WSE treated group and increased among those assigned to placebo (See, FIGS. 6-8B). In FIG. 6, these data were skewed, and the Mann Whitney U test showed no statistically significant differences between treatments. Clinical symptom improvements (PANSS or PSS) were not significantly correlated with S100B or hsCRP under WSE treatment. However, as shown in FIGS. 8A and 8B, for the two markers of inflammation, one from the brain (S100B) and the other that is a peripheral marker (hsCRP), it was shown that a decrease in hsCRP levels and a decrease in S100B levels are positively correlated (FIG. 8A) and this was seen only under WSE treatment (SENSORIL®, 0.621, p<0.001, n=30) but not under placebo treatment (FIG. 8B, –0.271, p<0.148, n=30).

Cytokines Over 90 percent (n=60) of the subjects had detectable IL-6 levels, whereas only 12%, 13.6% and 19.7% of the subjects had detectable IFN-γ, IL-4, and IL-2 levels respectively. Therefore, IL-6 was analyzed. The distribution of the IL-6 levels was right skewed and there were no statistically significant differences between the WSE and placebo groups (Mann-Whitney U test) (FIG. 7).

Weight, Body Mass Index (BMI) and Vital Signs are indicated in FIG. 9. At the end of the treatment period, WSE treated subjects gained a mean of 2.4 lbs. compared to 1.73 lbs. in the placebo group, and BMI increased by 0.33 mg/kg$^2$ in the WSE treated group vs. 0.20 mg/kg2 in the placebo group; both findings were statistically non-significant. Systolic and diastolic blood pressure readings, pulse, and temperature differences in the two treatment arms were not significantly different from baseline to end of the treatment period.

There were no statistically significant differences between treatments for adverse events that were reported at 5% in either group. The Data and Safety Monitoring Board classified these adverse events as mild to moderate, and they were all reported as transient (Table 6). Somnolence (21.1%), loose stool/diarrhea (18.1%), epigastric discomfort/stomach pain (9.1%), dry mouth (6.1%), hyperactivity (6.1%), rash (6.1%), and weight gain (6.1%) were more common in the WSE group, whereas headache (12.1%), anxiety (6.1%), and confusion (6.1%) were more common in the placebo group.

TABLE 6

Adverse Events Reported at ≥5% in Either Treatment Group

| Adverse Event | WSE n = 33 | | Placebo n = 33 | |
|---|---|---|---|---|
| | N | % | N | % |
| Gastrointestinal Disorders | | | | |
| loose stool/diarrhea | 6 | (18.1) | 5 | (15.5) |
| dry mouth | 2 | (6.1) | | |
| nausea | 2 | (6.1) | | |
| dyspepsia (heartburn) | 3 | (9.1) | 3 | (9.1) |
| epigastric discomfort/ stomach pain | 3 | (9.1) | 2 | (6.1) |
| Psychiatric Disorders | | | | |
| anxiety | | | 2 | (6.1) |
| hyperactive | 2 | (6.1) | | |
| confusion | | | 2 | (6.1) |
| worsening of psychiatric symptoms | 2 | (6.1) | 1 | (3.0) |
| Neurological/Nervous System Disorders | | | | |
| somnolence | 7 | (21.1) | 3 | (9.1) |
| headache | 2 | (6.1) | 4 | (12.1) |
| General Disorders | | | | |
| fatigue/lethargy | 2 | (6.1) | 2 | (6.1) |
| Skin Manifestations | | | | |
| rash | 2 | (6.1) | | |
| Metabolism and Nutrition | | | | |
| weight gain | 2 | (6.1) | 1 | (3.0) |

WSE = standardized extract of *Withania somnifera*

This study supports the hypothesis that a standardized extract of *W. somnifera*, when added adjunctively to antipsychotic medications, provides significant benefits for negative, general and total symptoms in patients with schizophrenia experiencing an exacerbation of symptoms. Patients receiving WSE also reported a significant diminution in their levels of perceived stress. Improvements with WSE treatment in negative, general and total symptoms were first noted at 4 weeks and continued through the 12 week study period. The relatively large treatment effects of WSE for negative, general and total symptoms of schizophrenia is especially encouraging given that a meta-analyses of adjunctive inflammatory agents, celecoxib and aspirin (eight studies), determined a significant but small treatment effect size for positive symptoms (Hedges' g=−0.189), and trend level treatment effect for total symptoms (Hedges' g=−0.236), but no benefit for negative symptoms of schizophrenia (Nitta M. et al.: Adjunctive Use of Nonsteroidal Anti-inflammatory Drugs for Schizophrenia: A Meta-analytic Investigation of Randomized Controlled Trials. *Schizophr Bull* 2013; 39:1230-1241). Even though improvements in positive symptom scores under WSE treatment was not significantly better than in the placebo group, however, there were significantly fewer anti-psychotic medication adjustments in the WSE group.

S100B is secreted by astrocytes and oligodendrocytes and is considered to be a marker of CNS inflammation. In the present study, even though declines in S100B levels with WSE and elevations in S100B with placebo were not significantly different between groups, WSE has known anti-inflammatory properties, including Cox-2 inhibition, suppression of NF-kB activation, and attenuation of pro-oxidant and inflammatory responses in microglial and astrocytic cells and enhancement of Nrf2/ARE reporter activity in astrocytes. In stressed animals, WSE enhances type-1 immunity, e.g., promotes normalization of IL-2 and IFN-γ levels and significantly improves anti-oxidant and lipid peroxidation indices. Furthermore, human studies have shown that WSE induces the proliferation of CD4+ and CD8+ T cells. WSE is also known to attenuate glutamate excitotoxicity; protect against deleterious propoxur induced anti-cholinergic brain and cognitive dysfunction; and recover dopamine levels and attenuate GFAP, a pro-inflammatory marker of astrocyte activation, in a mouse model of Parkinsonism. These separate lines of enquiry appear to point to WSE's favorable induction of type-1 cytokines and anti-inflammatory and anti-oxidant actions (Cox-2 inhibition, impact elevated S100B levels, others) in the CNS.

The data above support the potential of WSE to reverse the type-2/type-1 immunological dysfunction reported in schizophrenia.

In conclusion, WSE added adjunctively to antipsychotic medications in patients with schizophrenia experiencing an exacerbation of symptoms provides benefits for negative, general and total symptoms.

Example 2—Sensory and Cognitive Effects of WSE Administration to Patients with Schizophrenia As shown below, standardized extract of *W. somnifera*, when added to standard doses of marketed antipsychotic medications, improves event related brain potentials, specifically: mismatch negativity, P300, and gammaband, in addition to negative symptoms in persons with schizophrenia or schizoaffective disorder.

In the present example (n=11 subjects taken from the group of 66 patients of Example 1), some of the MMN deficit was recovered in persons with schizophrenia that were treated with WSE added to a standard anti-psychotic agent, compared to those subjects who received placebo, and the size of the WSE treatment effect for recovery of MMN was large (d=1.28). Furthermore this WSE treated group improved their negative symptoms scores significantly compared to those receiving placebo. Additionally, the WSE-treated group also improved on two other cortical neurophysiological deficits compared to the placebo group: the P300 ERP and the Gamma-band steady-state response. The size of the treatment effect of WSE was medium for Gamma band (d=0.59) compared to placebo (d=0.07). For P300, at the end of the treatment (12 weeks), the amplitude was larger for the attend condition in the WSE treated group (d=0.47) compared to placebo (d=0.24) and also for the ignore condition (WSE, d=0.69, placebo, d=0.29).

In further detail, eleven patients with Schizophrenia or Schizoaffective Disorder participated in a study to evaluate the effects of a standardized extract of *W. somnifera* (WSE) on Mismatch Negativity. These patients had experienced a recent exacerbation of symptoms and had been receiving standard antipsychotic agents for 4 weeks or longer. The standardized extract of *W. somnifera* (SENSORIL®) was added to anti-psychotic agents at a dosage of 250 mg twice a day for the first week (500 mg/day) and then increased to 500 mg twice a day (i.e. 1000 mg/day) for an additional 11 weeks. Mismatch negativity was measured before the patients received WSE and again at the end of the 12-week study. The study was designed as a randomized, double-blind, parallel arm, placebo-controlled clinical trial. Patients and research staff conducting the neurophysiology measurements (MMN) and the psychiatric rating scales (to measure improvements in psychopathology such as positive, negative, general or total symptoms using the Positive and Negative Syndrome Scale) were "blind" to whether patients were allocated to WSE or placebo. Similarly, the analyses of MMN and the clinical variables (i.e. PANSS positive, negative, general and total symptoms) were undertaken "blind" to treatment allocation.

Event related potential (ERPs) were measured, including MMN, P300, and Gamma-band. Participants watched a silent movie, and ignored repeated tones (50 ms, 1.2 kHz, 10%) interspersed with pitch (100 ms, 1 kHz, 10%) in a MMN task, and completed two auditory oddball tasks, either counting rare pitch duration deviants (50 ms, 1.2 kHz, 15%) or ignoring all sounds. These ERPs were measured before participants received drug or placebo and at the end of the double-blind study.

TABLE 7 demographic and illness characteristics of the 11 patients. Five patients were randomly assigned to WSE and six patients to placebo.

|  | WSE (n = 5) | Placebo (n = 6) |
|---|---|---|
| Diagnosis, Schizophrenia/Schizoaffective, n | 3/2 | 2/4 |
| Age, mean (SD), y | 45 (11.07) | 47.33 (11.52) |
| Gender, male/female, n | 1/4 | 3/3 |
| Age at onset of 1$^{st}$ episode, mean (SD), y | 22.8 (14.9) | 24 (11.09) |
| Duration of illness, mean (SD), y | 22.2 (14.38) | 23.3 (11.98) |
| Number of lifetime psychiatric hospitalizations, mean (SD) | 7.2 (2.8) | 7.8 (6.8) |
| Atypical Antipsychotics, n | 5 | 5 |
| OLZ Equivalent mean (SD), mg/day | 16.8 (12.85) | 15.52 (9.39) |
| Typical Antipsychotics, n | 0 | 1 |

WSE—Standardized extract of *Withania somnifera* (SENSORIL ®), SD—standard deviation, n—number, y—years, OLZ Equivalent—all anti-psychotic drugs converted to olanzapine in mg/day using the antipsychotic conversion website found here: Leucht S, Samara M, Heres S, et al. Dose Equivalents for Antipsychotic Drugs: The DDD Method. Schizophr Bull. 2016; (42): S90-S94

As can be seen from FIG. 10A, treatment with WSE appeared to recover some of the mismatch negativity (MMN) deficit observed at T1 (before treatment), reflected in trend-level ($p<0.09$) improvements (large treatment effect) in duration-deviant MMN with WSE ($d=1.28$) but not with placebo at T2 (end of 12 weeks of treatment) ($d=-0.27$, see FIG. 10A T2 in red, black arrow). An effect size—"d">1 is typically considered a "large treatment effect" (Cohen J. Quantitative Methods in Psychology, A Power Primer. Psychological Bulletin, 1992, Vol. 112. No. 1, 155-159). Importantly, in this group of 11 patients, negative symptom scores improved significantly under WSE treatment vs. placebo (mean±standard deviation (SD) change scores: 4±2.24 for WSE vs. 0.33±1.97 for placebo, Mann-Whitney U 3.0, $p<0.03$). Expressed as percentage change in negative symptom scores from before to end of treatment, the 5 patients treated with WSE improved by 22.49% (±11.58) vs. 3.20% (±12.62) (Table 8) for placebo (Mann-Whitney U=4, $p<0.046$), statistical significance was determined by a two-tailed test.

TABLE 8

Percentage Change in PANSS Scores

| | WSE | | | | | Placebo | | | |
|---|---|---|---|---|---|---|---|---|---|
| ID | PANSS Positive | PANSS Negative | PANSS General | PANSS Total | ID | PANSS Positive | PANSS Negative | PANSS General | PANSS Total |
| 50 | 25.93% | 5.26% | 0% | 10.39% | 48 | -11.11% | -4.55% | -11.76% | -9.64% |
| 54 | 30.00% | 25.93% | 21.62% | 25.00% | 49 | 25.00% | 11.11% | 18.92% | 19.35% |
| 56 | 28.57% | 16.67% | 30% | 26.39% | 51 | 8.10% | 12.50% | 22.22% | 25.00% |
| 61 | 31.58% | 31.25% | 0% | 18.03% | 58 | 21.05% | -13.33% | 23.33% | 14.06% |
| 64 | 22.22% | 33.33% | 0% | 12.90% | 59 | 3.33% | 18.75% | 13.79% | 20.63% |
| | | | | | 63 | 6.67% | -5.26% | 0% | 0% |

A negative symbol (−) indicates worsening of symptoms

Improvements favoring the WSE treated group (vs. placebo) were also noted for P300 and Gamma band steady state potentials, FIG. 10B. In the oddball task, the WSE treated group showed a larger P300 from before treatment (T1) to end of treatment—T2 (attend task: $d=0.47$; ignore: $d=0.69$) compared to placebo (attend task, $d=0.24$, ignore, $d=0.29$). Gamma-band steady state potentials in the WSE group displayed greater attention-related amplitude increase at T2 ($d=0.59$) than in the placebo group ($d=0.07$). FIG. 10C.

The following clauses provide various, non-limiting aspects of the invention.

1. A method of treating a psychiatric disorder for which an antipsychotic drug is administered in a patient, comprising administering to the patient a *Withania somnifera* active agent in combination with an antipsychotic active agent in amounts effective to treat the psychiatric disorder.

2. The method of clause 1, wherein the psychiatric disorder is a psychotic disorder, such as schizophrenia or a schizoaffective disorder.

3. The method of clause 1, wherein the psychiatric disorder is selected from the group consisting of: schizophrenia; Schizophrenia, Paranoid Type; Schizophrenia, Disorganized Type; Schizophrenia, Undifferentiated Type; Schizophrenia, Residual Type; Schizoaffective Disorder; Schizophreniform Disorder; Delusional Disorder; Brief Psychotic Disorder; Other specified Schizophrenia Spectrum and other Psychotic Disorder; Unspecified Schizophrenia Spectrum, and other Psychotic Disorder.

4. The method of clause 2 or 3, wherein a negative symptom of the psychiatric disorder is improved in the patient after administration of the *W. somnifera* active agent to the patient.

5. The method of clause 2 or 3, wherein stress symptoms, depression, anxiety, and/or excitation symptoms of the psychiatric disorder is improved in the patient after administration of the *W. somnifera* active agent to the patient.

6. The method of clause 2 or 3, wherein a sensory or cognitive symptom of the psychiatric disorder is improved in the patient after administration of the *W. somnifera* active agent to the patient.

7. The method of clause 6, wherein the sensory or cognitive symptom is an electroencephalogram response to an auditory stimulus.

8. The method of clause 6, wherein the electroencephalogram response is one or more of a mismatch negativity abnormality, a P300 event-related potential, or a gammaband auditory steady state response.

9. The method of clause 1, wherein the *W. somnifera* active agent is provided in leaves and/or roots of a *Withania somnifera* plant or an extract of plant material, for example roots and/or leaves of a *W. somnifera* plant.

10. The method any of one of clauses 1-9, wherein leaves and/or roots of a *Withania somnifera* plant or an extract of, the roots and/or leaves of, a *W. somnifera* plant, or a *W. somnifera* active agent, are administered in an amount effective to treat one or more negative symptoms of the psychiatric disorder.

11. The method of clause 1, wherein the *W. somnifera* active agent is administered to the patient orally.

12. The method of clause 1 or 2, wherein the *W. somnifera* active agent is administered to the patient for at least four weeks, and optionally indefinitely.

13. The method of any one of clauses 1-12, wherein the *W. somnifera* active agent is provided in a standardized extract comprising:
   a. at least 3% (% wt.) of withanolide glycosides and sitoindosides;
   b. at least 3% of oligosaccharides; and
   c. less than 0.5% of free withaferin A (aglycone),
   wherein (a):(c) is 75-95:25-5 and (a):(b) is 40-60:60-40.

14. The method of clause 13, wherein the standardized extract comprises:
   a. at least 8% of withanolide glycosides and sitoindosides; and
   b. at least 32%, of oligosaccharides.

15. The method of clause 13 or 14, wherein the oligosaccharide has a weight average molecular weight (Mw) of less than 2000 Da.

16. The method of clause 13, wherein the standardized extract comprises at least 8% wt. total withanolide glycoside conjugates, 2% wt. or less withaferin A, and a ratio of withanolide glycoside conjugates to free withaferin A ranging from 75:95 to 25:5, optionally with % wt. determined by high performance liquid chromatography (HPLC).

17. The method of any one of clauses 1-16, wherein the *W. somnifera* active agent is administered to the patient for at least four weeks in an amount of from 100 mg to 2000 mg twice daily.

18. The method of clause 16, wherein the *W. somnifera* active agent is administered to the patient in an amount of 250 mg twice daily for the first week, and up to 500 mg twice daily thereafter.

19. The method of any one of clauses 1-18, wherein the *W. somnifera* active agent is a withanolide glycoside or sitoindoside, or an aglycone derivative thereof.

20. The method of clause 19, wherein the *W. somnifera* active agent includes one or more of withanolide D, sitoindoside VII, sitoindoside VIII, sitoindoside IX, and sitoindoside X.

21. The method of any one of clauses 1-18, wherein the *W. somnifera* active agent comprises:

where $R^1$ is H, $C_1$-$C_3$ alkyl, or $C_1$-$C_4$ alkoxyl, $R^2$ is H or $C_1$-$C_3$ alkyl, $R^3$ is H or HO, and ≡≡≡≡≡ is a single or double bond.

22. A pharmaceutical dosage form, or a composition, for use in treatment of a psychiatric disorder for which an antipsychotic drug is administered, comprising an antipsychotic agent and a *Withania somnifera* active agent in amounts effective to treat the psychiatric disorder, such as a psychotic disorder, such as schizophrenia or schizoaffective disorder, and optionally one or more negative symptoms of the psychiatric disorder.

23. The pharmaceutical dosage form of clause 22, wherein the *W. somnifera* active agent is provided as leaves and/or roots of a *W. somnifera* plant or as an extract of roots and/or leaves of a *W. somnifera* plant.

24. The pharmaceutical dosage form of clause 22, prepared as an oral or parenteral dosage form.

25. The pharmaceutical dosage form of clause 22, comprising from 100 mg to 2000 mg per dose, e.g., 250 mg, 500 mg, or 1000 mg per dose, of an extract of roots and/or leaves of a *W. somnifera* plant.

26. The pharmaceutical dosage form of clause 25, wherein the *W. somnifera* active agent is provided in a standardized extract comprising:
   a. at least 3% (% wt.) of withanolide glycosides and sitoindosides;
   b. at least 3% 3-8%, of oligosaccharides; and
   c. less than 0.5% of free withaferin A (aglycone),
   wherein (a):(c) is 75-95:25-5 and (a):(b) is 40-60:60-40.

27. The pharmaceutical dosage form of clause 26, wherein the standardized extract comprises:
   a. at least 8% of withanolide glycosides and sitoindosides; and
   b. at least 32%, of oligosaccharides.

28. The pharmaceutical dosage form of clause 26 or 27, wherein the oligosaccharide has a weight average molecular weight (Mw) of less than 2000 Da.

29. The pharmaceutical dosage form of clause 26, wherein the standardized extract comprises at least 8% wt. total withanolide glycoside conjugates, 2% wt. or less withaferin A, and a ratio of withanolide glycoside conjugates to free withaferin A ranging from 75:95 to 25:5, optionally with % wt. determined by high performance liquid chromatography (HPLC).

30. The pharmaceutical dosage form of clause 22, wherein the *W. somnifera* active agent comprises a withanolide glycoside or sitoindoside, or an aglycone derivative thereof.

31. The pharmaceutical dosage form of clause 30, wherein the *W. somnifera* active agent comprises: withanolide D, sitoindoside VII, sitoindoside VIII, sitoindoside IX, sitoindoside X, derivatives thereof, or any combination thereof.

32. The pharmaceutical dosage form of clause 22, wherein the *W. somnifera* active agent comprises:

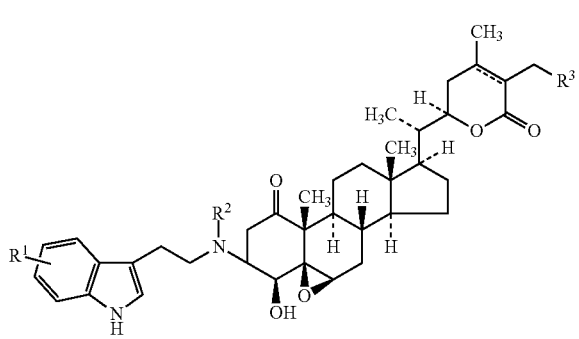

where $R^1$ is H, $C_1$-$C_3$ alkyl, or $C_1$-$C_4$ alkoxyl, $R^2$ is H or $C_1$-$C_3$ alkyl, $R^3$ is H or HO, and ═════ is a single or double bond.

33. A *Withania somnifera* active agent for use in the treatment of a negative symptom of a psychiatric disorder.

34. The *W. somnifera* active agent of clause 33, wherein the *W. somnifera* active agent is provided as leaves and/or roots of a *W. somnifera* plant or as an extract of roots and/or leaves of a *W. somnifera* plant.

35. The *W. somnifera* active agent of clause 33, prepared as an oral or parenteral dosage form.

36. The *W. somnifera* active agent of clause 33, comprising from 100 mg to 2000 mg per dose, e.g., 250 mg, 500 mg, or 1000 mg per dose, of an extract of roots and/or leaves of a *W. somnifera* plant.

37. The *W. somnifera* active agent of clause 33, wherein the *W. somnifera* active agent is provided in a standardized extract comprising:
  a. at least 3% (% wt.) of withanolide glycosides and sitoindosides;
  b. at least 3% of oligosaccharides; and
  c. less than 0.5% of free withaferin A (aglycone),
wherein (a):(c) is 75-95:25-5 and (a):(b) is 40-60:60-40.

38. The *W. somnifera* active agent of clause 37, wherein the standardized extract comprises:
  a. at least 8% of withanolide glycosides and sitoindosides; and
  b. at least 32%, of oligosaccharides.

39. The *W. somnifera* active agent of clause 37 or 38, wherein the oligosaccharide has a weight average molecular weight (Mw of less than 2000 Da.

40. The *W. somnifera* active agent of clause 37, wherein the standardized extract comprises at least 8% wt. total withanolide glycoside conjugates, 2% wt. or less withaferin A, and a ratio of withanolide glycoside conjugates to free withaferin A ranging from 75:95 to 25:5, optionally with % wt. determined by high performance liquid chromatography (HPLC).

41. The *W. somnifera* active agent of clause 33, wherein the *W. somnifera* active agent is a withanolide glycoside or sitoindoside, or an aglycone derivative thereof.

42. The *W. somnifera* active agent of clause 41, wherein the *W. somnifera* active agent comprises withanolide D, sitoindoside VII, sitoindoside VIII, sitoindoside IX, sitoindoside X, derivatives thereof, or any combination thereof.

43. The *W. somnifera* active agent of clause 32, comprising:

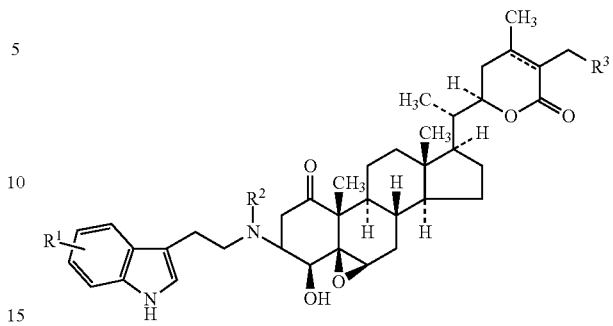

where $R^1$ is H, $C_1$-$C_3$ alkyl, or $C_1$-$C_4$ alkoxyl, $R^2$ is H or $C_1$-$C_3$ alkyl, $R^3$ is H or HO, and ═════ is a single or double bond.

44. The *W. somnifera* active agent of clause 32, wherein the psychiatric disorder is a psychotic disorder, such as schizophrenia or a schizoaffective disorder.

45. The *W. somnifera* active agent of clause 32, wherein the psychiatric disorder is selected from the group consisting of: schizophrenia; Schizophrenia, Paranoid Type; Schizophrenia, Disorganized Type; Schizophrenia, Undifferentiated Type; Schizophrenia, Residual Type; Schizoaffective Disorder; Schizophreniform Disorder; Delusional Disorder; Brief Psychotic Disorder; Other specified Schizophrenia Spectrum and other Psychotic Disorder; Unspecified Schizophrenia Spectrum, and other Psychotic Disorder.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

What is claimed is:

1. A method of treating one or more negative symptoms of schizophrenia or schizoaffective disorder in a patient exhibiting a mismatch negativity abnormality, comprising administering to the patient having the one or more negative symptoms of schizophrenia or schizoaffective disorder a *Withania somnifera* active agent in combination with an antipsychotic active agent, wherein the *Withania somnifera* active agent is administered for at least four weeks in an amount of from 1000 mg to 2000 mg daily, and wherein the combination of the *Withania somnifera* active agent and the antipsychotic active agent treats the one or more negative symptoms of schizophrenia or schizoaffective disorder in the patient; and
  assessing mismatch negativity in the patient, wherein administering the *Withania somnifera* active agent in combination with the antipsychotic active agent ameliorates the mismatch negativity abnormality.

2. The method of claim 1, wherein the *W. somnifera* active agent is provided in leaves or roots of a *Withania somnifera* plant or an extract of plant material.

3. The method of claim 1, wherein the *W. somnifera* active agent is administered to the patient orally.

4. The method of claim 1, wherein the *W. somnifera* active agent is provided in a standardized extract comprising:
  a. at least 3% (% wt.) of withanolide glycosides and sitoindosides;
  b. at least 3% (% wt.) of oligosaccharides; and
  c. less than 0.5% (% wt.) of free withaferin A (aglycone), wherein (a):(c) is 75-95:25-5 and (a):(b) is 40-60:60-40.

5. The method of claim 4, wherein the standardized extract comprises at least 8% wt. total withanolide glycoside conjugates, 2% wt. or less withaferin A, and a ratio of withanolide glycoside conjugates to free withaferin A ranging from 75:95 to 25:5, optionally with % wt. determined by high performance liquid chromatography (HPLC).

6. The method of claim 1, wherein the *W. somnifera* active agent is a withanolide glycoside or sitoindoside, or an aglycone derivative thereof.

7. The method of claim 1, wherein the *W. somnifera* active agent includes one or more of withanolide D, sitoindoside VII, sitoindoside VIII, sitoindoside IX, sitoindoside X, and a compound having the structure:

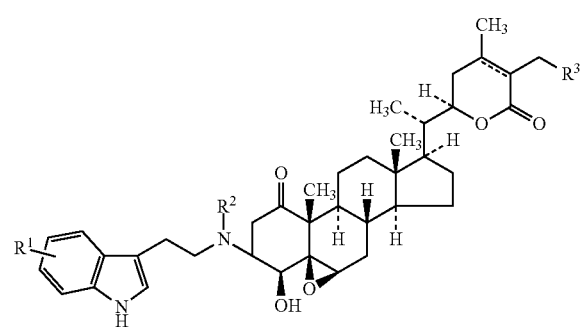

where R1 is H, C1-C3 alkyl, or C1-C4 alkoxyl, R2 is H or C1-C3 alkyl, R3 is H or HO, and is a single or double bond.

8. The method of claim 1, wherein an electroencephalogram response to an auditory stimulus, a P300 event-related potential, or a gammaband auditory steady state response is improved in the patient after administration of the *W. somnifera* active agent to the patient for twelve weeks.

9. The method of claim 2, wherein the *W. somnifera* active agent is provided in leaves and roots of a *W. somnifera* plant.

10. The method of claim 4, wherein the oligosaccharide has a weight average molecular weight (Mw) of less than 2000 Da.

11. The method of claim 1, wherein the *W. somnifera* active agent is provided in a standardized extract comprising:
   a. at least 8% (% wt.) of withanolide glycosides and sitoindosides;
   b. at least 32% (% wt.) of oligosaccharides; and
   c. less than 0.5% (% wt.) of free withaferin A (aglycone), wherein (a):(c) is 75-95:25-5 and (a):(b) is 40-60:60-40.

12. A method of treating one or more negative symptoms of schizophrenia or schizoaffective disorder in a patient exhibiting a mismatch negativity abnormality, comprising:
   administering to the patient having the one or more negative symptoms of schizophrenia or schizoaffective disorder:
   a first active agent consisting of a *Withania somnifera* active agent; and
   a second active agent comprising an antipsychotic active agent; and
   assessing mismatch negativity in the patient,
   wherein the *Withania somnifera* active agent is administered for at least four weeks in an amount of from 100 mg to 2000 mg twice daily,
   wherein the combination of the *Withania somnifera* active agent and the antipsychotic active agent treats the one or more negative symptoms of schizophrenia or schizoaffective disorder in the patient, and
   wherein administering the *Withania somnifera* active agent in combination with the antipsychotic active agent ameliorates the mismatch negativity abnormality.

13. A method of treating one or more negative symptoms of schizophrenia or schizoaffective disorder in a patient, comprising:
   administering to the patient having the one or more negative symptoms of schizophrenia or schizoaffective disorder a *Withania somnifera* active agent in combination with an antipsychotic active agent; and
   assessing mismatch negativity in the patient,
   wherein the *Withania somnifera* active agent is administered for at least four weeks in an amount of from 100 mg to 2000 mg twice daily,
   wherein the combination of the *Withania somnifera* active agent and the antipsychotic active agent treats the one or more negative symptoms of schizophrenia or schizoaffective disorder in the patient, and
   wherein a mismatch negative abnormality in an electroencephalogram response to an auditory stimulus is improved after administration of the *W. somnifera* active agent to the patient having the one or more negative symptoms of schizophrenia or schizoaffective disorder.

14. The method of claim 1, wherein the *Withania somnifera* active agent is administered for at least twelve weeks.

15. The method of claim 12, wherein the *Withania somnifera* active agent is administered for at least twelve weeks in an amount of 250 mg to 1000 mg twice daily.

16. The method of claim 12, wherein the *Withania somnifera* active agent is administered for one week in an amount of 250 mg twice daily, and is thereafter administered in an amount of 500 mg twice daily for at least eleven weeks.

17. The method of claim 13, wherein the *Withania somnifera* active agent is administered for at least twelve weeks in an amount of 250 mg to 1000 mg twice daily.

18. The method of claim 13, wherein the *Withania somnifera* active agent is administered for one week in an amount of 250 mg twice daily, and is thereafter administered in an amount of 500 mg twice daily for at least eleven weeks.

* * * * *

UNITED STATES PATENT AND TRADEMARK OFFICE
CERTIFICATE OF CORRECTION

| | | |
|---|---|---|
| PATENT NO. | : 11,219,659 B2 | Page 1 of 1 |
| APPLICATION NO. | : 15/775565 | |
| DATED | : January 11, 2022 | |
| INVENTOR(S) | : Chengappa et al. | |

It is certified that error appears in the above-identified patent and that said Letters Patent is hereby corrected as shown below:

On the Title Page

Column 2, Line 5, under item (56), Other Publications, delete "Consituents" and insert
-- Constituents --

Column 2, Line 14, under item (56), Other Publications, delete "Aswagandha" and insert
-- Ashwagandha --

In the Claims

Column 25, Line 29, Claim 7, delete "where R1 is H, C1-C3 alkyl, or C1-C4 alkoxyl, R2 is H or C1-C3 alkyl, R3 is H or HO, and is a single or double bond." and insert -- where $R^1$ is H, $C_1$-$C_3$ alkyl, or $C_1$-$C_4$ alkoxyl, $R^2$ is H or $C_1$-$C_3$ alkyl, $R^3$ is H or HO, and  is a single or double bond. --

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*